(12) United States Patent
Yagi

(10) Patent No.: US 12,741,132 B2
(45) Date of Patent: Sep. 22, 2026

(54) ACCESS PORT

(71) Applicant: Toray Industries, Inc., Tokyo-to (JP)

(72) Inventor: Takahiro Yagi, Otsu (JP)

(73) Assignee: Toray Industries, Inc., Tokyo (JP)

( * ) Notice: Subject to any disclaimer, the term of this patent is extended or adjusted under 35 U.S.C. 154(b) by 1000 days.

(21) Appl. No.: 17/785,107

(22) PCT Filed: Feb. 3, 2021

(86) PCT No.: PCT/JP2021/003854
§ 371 (c)(1),
(2) Date: Jun. 14, 2022

(87) PCT Pub. No.: WO2021/166643
PCT Pub. Date: Aug. 26, 2021

(65) Prior Publication Data

US 2023/0025137 A1 Jan. 26, 2023

(30) Foreign Application Priority Data

Feb. 17, 2020 (JP) ................................ 2020-024533

(51) Int. Cl.
*A61M 39/02* (2006.01)
*A61M 25/00* (2006.01)

(52) U.S. Cl.
CPC .... *A61M 39/0247* (2013.01); *A61M 25/0097* (2013.01); *A61M 2039/0258* (2013.01); *A61M 2039/0282* (2013.01)

(58) Field of Classification Search
CPC ...... A61M 2039/0081; A61M 39/0208; A61M 2039/0229; A61M 39/0247;
(Continued)

(56) References Cited

U.S. PATENT DOCUMENTS 4,364,395 A * 12/1982 Redmond ........... A61M 27/006 604/10
4,710,167 A 12/1987 Lazorthes
(Continued)

FOREIGN PATENT DOCUMENTS

CN 104640599 A 5/2015
CN 205095225 U 3/2016
(Continued)

OTHER PUBLICATIONS

International Search Report dated Apr. 20, 2021 in counterpart International Application No. PCT/JP2021/003854.
(Continued)

*Primary Examiner* — Emily L Schmidt
*Assistant Examiner* — Samuel J Marrison
(74) *Attorney, Agent, or Firm* — DLA Piper LLP (US)

(57) ABSTRACT

An access port can be connected to a catheter and includes a port body including a liquid storage portion and a diaphragm body covering the liquid storage portion. The port body includes a connection passage connected to the liquid storage portion and allows the liquid storage portion to communicate with the inside of the catheter. In the cross-section along the axial direction of the connection passage at the connection position where the connection passage is connected to the liquid storage portion, the length in the direction perpendicular to the axial direction between the surface of the diaphragm body on the side opposite to the liquid storage portion and the inner surface of the liquid storage portion gradually decreases as it proceeds away from the connection position in the inclined region exceeding half of the liquid storage portion along the axial direction.

10 Claims, 16 Drawing Sheets

(58) Field of Classification Search
CPC .. A61M 2039/0261; A61M 2039/0232; A61M 2039/0226; A61M 2039/0238
See application file for complete search history.

(56) References Cited

U.S. PATENT DOCUMENTS

| | | | | |
|---|---|---|---|---|
| 5,263,930 | A * | 11/1993 | Ensminger | A61M 39/0606 604/288.03 |
| 7,351,233 | B2 | 4/2008 | Parks | |
| 2004/0199220 | A1 | 10/2004 | Cantlon | |
| 2007/0219510 | A1* | 9/2007 | Zinn | A61M 39/0208 604/288.01 |
| 2009/0105688 | A1 | 4/2009 | McIntyre et al. | |
| 2009/0306606 | A1 | 12/2009 | Lancette et al. | |
| 2011/0004167 | A1* | 1/2011 | Ko | A61M 39/0208 604/288.01 |
| 2011/0251563 | A1 | 10/2011 | Ko et al. | |
| 2012/0083751 | A1 | 4/2012 | Dalton | |
| 2013/0035648 | A1* | 2/2013 | Ko | A61M 39/0208 604/288.01 |
| 2014/0207086 | A1 | 7/2014 | Stats et al. | |
| 2015/0190623 | A1 | 7/2015 | Ueda et al. | |
| 2019/0314569 | A1* | 10/2019 | Young | A61M 1/3655 |
| 2020/0061362 | A1* | 2/2020 | Singh | C12N 15/861 |

FOREIGN PATENT DOCUMENTS

| | | | |
|---|---|---|---|
| JP | S61-265146 | A | 11/1986 |
| JP | 3142990 | U | 7/2008 |
| JP | 2016-504158 | A | 2/2016 |
| JP | 2017-12481 | A | 1/2017 |
| JP | 6057916 | B2 | 1/2017 |
| WO | 2019160226 | A1 | 8/2019 |

OTHER PUBLICATIONS

Written Opinion dated Apr. 20, 2021 in counterpart International Application No. PCT/JP2021/003854.

Office Action dated Sep. 28, 2023, of counterpart Chinese Patent Application No. 202180015140.4, along with an English translation.

Examination Report dated Aug. 23, 2023, of counterpart Indian Patent Application No. 202247051512.

Supplementary Partial European Search Report dated Feb. 29, 2024, from counterpart European Application No. 21757266.8.

Office Action dated Oct. 11, 2023, of counterpart Taiwanese Patent Application No. 110104917, along with an English translation.

Extended European Search Report dated May 7, 2024, from counterpart European Patent Application No. 21757266.8.

Office Action dated Apr. 18, 2025, from counterpart Korean Patent Application No. 10-2022-7008725.

Notice of Reasons for Refusal dated Jun. 25, 2024, of counterpart Japanese Patent Application No. 2021-506595, along with an English machine translation.

Written Opinion dated Mar. 12, 2026, from counterpart Singapore Application No. 11202250910G.

Official Action dated Jul. 10, 2026, from counterpart European Application No. 21757266.8.

* cited by examiner

ACCESS PORT

TECHNICAL FIELD

This disclosure relates to an access port.

BACKGROUND

Treatment using a catheter indwelled in the body of a patient is popularly performed because administration of a drug or the like can be performed from the vicinity of a target lesion. One end of the catheter is connected to an access port embedded under the skin of the patient, and the other end is disposed in the vicinity of the target lesion. The lumen of the access port and the lumen of the catheter are connected by a connection passage, and when a drug is introduced into the lumen of the access port, the drug can be carried to the vicinity of a target lesion through the connection passage and the catheter. For example, JP 6057916 B2 discloses an access port used with a catheter.

It is desirable to pass a microcatheter having a smaller diameter into a catheter indwelled in the body of a patient, advance the tip of the microcatheter to a peripheral blood vessel region, and administer a drug or the like from the further vicinity of a target lesion. In that instance, as a method of passing the microcatheter into the catheter, it is possible to first puncture the diaphragm of the access port using a puncture needle, and insert the microcatheter into the lumen of the catheter through the lumen of the puncture needle, the lumen of the access port, and the connection passage. Alternatively, it is possible to first insert a guide wire that is thinner and stiffer than the microcatheter into the lumen of the catheter through the lumen of the puncture needle, the lumen of the access port, and the connection passage, and insert the microcatheter into the lumen of the catheter using the guide wire as a guide.

When the microcatheter or the guide wire is inserted into the lumen of the catheter, the access port and the catheter are embedded under the skin of the patient. Therefore, neither the tip of the microcatheter or the guide wire nor the connection passage can be directly observed. Therefore, the position of the connection passage is searched while rotating the tip by operating the microcatheter or the guide wire.

However, in such a method, the microcatheter and the guide wire cannot be stably and easily inserted into the connection passage.

It could therefore be helpful to provide an access port enabling a microcatheter or a guide wire to be stably and easily inserted into a connection passage.

SUMMARY

An access port used by being connected to a catheter, the access port including: a port body including a liquid storage portion; and a diaphragm body that is held by the port body and covers the liquid storage portion, in which the port body includes a connection passage connected to the liquid storage portion to allow the liquid storage portion to communicate with an inside of the catheter, and in a cross-section along an axial direction of the connection passage at a connection position where the connection passage is connected to the liquid storage portion, a length in a direction perpendicular to the axial direction between a surface of the diaphragm body opposite to the liquid storage portion and an inner surface of the liquid storage portion gradually decreases as it proceeds away from the connection position in an inclined region exceeding half of the liquid storage portion along the axial direction.

The inclined region may include a half region of the liquid storage portion on the side away from the connection position.

In the cross-section along the axial direction of the connection passage, the inner surface of the liquid storage portion in the inclined region may be inclined with respect to the axial direction toward the side away from the diaphragm body as it approaches the connection position in the axial direction.

The inner surface of the port body may include a bottom surface that forms (defines) the liquid storage portion and a side surface that extends from the bottom surface to form (define) the liquid storage portion, and the bottom surface may be inclined with respect to the axial direction toward the side away from the diaphragm body as it approaches the connection position in the axial direction.

The bottom surface of the port body may include a connection bottom surface connected to a side wall surface to which the connection passage is open, and a main bottom surface located on the side away from the connection position with respect to the connection bottom surface in the axial direction, the main bottom surface may be inclined with respect to the axial direction toward the side away from the diaphragm body as it approaches the connection position, and the connection bottom surface may be inclined with respect to the axial direction toward the side closer to the diaphragm body as it approaches the connection position.

The port body may have a bottom wall portion that forms a bottom surface of the liquid storage portion, and a thickness of the bottom wall portion may gradually decrease as it approaches the connection position along the axial direction.

The port body may include a bottom wall portion that forms a bottom surface of the liquid storage portion and a side wall portion that forms a side surface of the liquid storage portion, the side wall portion may include a protruding portion provided to be spaced apart from the bottom wall portion and having a facing guide surface facing the bottom surface, and the connection passage may open to the side surface at a position between the facing guide surface and the bottom surface.

The facing guide surface may have a concave surface recessed away from the bottom surface at a central portion in a width direction perpendicular to both the axial direction and a direction in which the facing guide surface faces the bottom surface.

The concave surface may be connected to a wall surface that forms (defines) the connection passage.

The inner surface of the port body may include a connection bottom surface provided at a position facing the facing guide surface, and a main bottom surface located on the side away from the connection position with respect to the connection bottom surface in the axial direction, the main bottom surface may be inclined with respect to the axial direction toward the side away from the diaphragm body as it approaches the connection position, and the connection bottom surface may be inclined with respect to the axial direction toward the side closer to the diaphragm body as it approaches the connection position.

The port body may include a bottom wall portion that forms a bottom surface of the liquid storage portion and a side wall portion that extends from the bottom wall portion to form a side surface of the liquid storage portion, the side wall portion may include a pair of flat wall portions provided side by side in a circumferential direction, the connection passage may be open to the side surface at a position between the pair of flat wall portions, and the pair of flat wall portions may form a tapered side surface that extends linearly and is tapered toward the connection passage when observed from a direction parallel to a direction in which the side wall portion extends from the bottom wall portion.

The port body may include a bottom wall portion that forms a bottom surface of the liquid storage portion and a side wall portion that extends from the bottom wall portion to form a side surface of the liquid storage portion, the side wall portion may include a pair of flat wall portions arranged side by side in a circumferential direction, the connection passage may be open to the side surface at a position between the pair of flat wall portions, and the bottom wall portion may include a guide rib extending linearly toward the connection position when observed from a direction parallel to a direction in which the side wall portion extends from the bottom wall portion.

The port body may include a bottom wall portion that forms a bottom surface of the liquid storage portion, and a side wall portion that extends from the bottom wall portion and forms a side surface of the liquid storage portion, the diaphragm body may include an annular holding groove that extends in a direction parallel to a direction in which the side wall portion extends from the bottom wall portion and is open to the side opposite to the liquid storage portion, and the port body may include an annular holding protrusion portion that protrudes in the direction parallel to the direction in which the side wall portion extends from the bottom wall portion.

The port body may include a base member that forms a bottom surface and a side surface of the liquid storage portion, and a lid member that is fixed to the base member so that the diaphragm body is held between the base member and the lid member, the base member may include a bottom member that forms at least the bottom surface, and an annular member that is supported by the bottom member to surround the liquid storage portion, and the annular member may include a protruding portion that is provided to correspond to the connection position and protrude toward the liquid storage portion.

The annular member may be made of an X-ray opaque material.

The port body may include a surface layer member that forms the inner surface of the liquid storage portion and the connection passage, and the surface layer member may connect the inner surface of the liquid storage portion and the connection passage seamlessly.

The surface layer member may be made of metal.

An inner surface of the liquid storage portion may have a funnel shape.

In a cross-section perpendicular to the axial direction of the connection passage, an inner surface of the port body may be inclined with respect to a lower surface of the diaphragm body facing the inner surface of the port body to approach the diaphragm body on both outer sides in a direction along the lower surface.

The inner surface may extend in a U-shape in the cross-section perpendicular to the axial direction of the connection passage.

The bottom surface may extend in parallel to the axial direction in a cross-section along the axial direction of the connection passage passing through the connection position.

In the cross-section along the axial direction of the connection passage, a surface of the diaphragm body opposite to the liquid storage portion may be inclined with respect to the axial direction.

A surface of the diaphragm body opposite to the liquid storage portion may have a first surface located on a side away from the connection position in the axial direction, and a second surface located on a side closer to the connection position in the axial direction with respect to the first surface and inclined with respect to the first surface, a length of the first surface along the axial direction may be longer than a length of the second surface along the axial direction, the first surface may be inclined with respect to the axial direction toward a side away from the inner surface of the liquid storage portion as it approaches the connection position in the axial direction, and an inclination angle of the first surface with respect to the axial direction may be larger than an inclination angle of the second surface with respect to the axial direction.

The port body may have a built-in metal coil.

The port body may include at least two metal coils provided to be spaced apart from each other at positions around the liquid storage portion.

A surface of the diaphragm body opposite to the liquid storage portion may be exposed to a region between the two metal coils.

The port body may include at least two light emitters electrically connected to the metal coils.

The light emitting surfaces of the at least two light emitters may be exposed.

The port body may include a bottom wall portion that forms a bottom surface of the liquid storage portion and a side wall portion that forms a side surface of the liquid storage portion, and the at least two metal coils may be incorporated in the side wall portion.

An axis of each metal coil may extend in a direction parallel to a direction in which the side wall portion extends from the bottom wall portion.

It is thus possible to provide an access port that enables a microcatheter or a guide wire to be stably and easily inserted into the connection passage.

REFERENCE SIGNS LIST

| | |
|---|---|
| 10 and 100 | Access port |
| 11 and 111 | Port body |
| 11a | Liquid storage portion |
| 11b | Bottom surface |
| 11c | Side surface |
| 11d | Connection bottom surface |
| 11e | Main bottom surface |
| 12 | Base member |
| 13 | Bottom member |
| 14 | Annular member |
| 20 | Bottom wall portion |
| 21 | Guide rib |
| 30 | Side wall portion |
| 31 | Protruding portion |
| 31a | Facing guide surface |
| 31b | Concave surface |
| 32 | Flat wall portion |
| 40 | Connection passage |
| 40a | Wall surface |
| 50 and 150 | Lid member |
| 60 and 160 | Diaphragm body |
| 70, 70a and 70b | Metal coil |
| 71, 71a and 71b | Light emitter |
| 115 | Surface layer member |
| 160c | First surface |
| 160d | Second surface |

DETAILED DESCRIPTION

Figure 1:
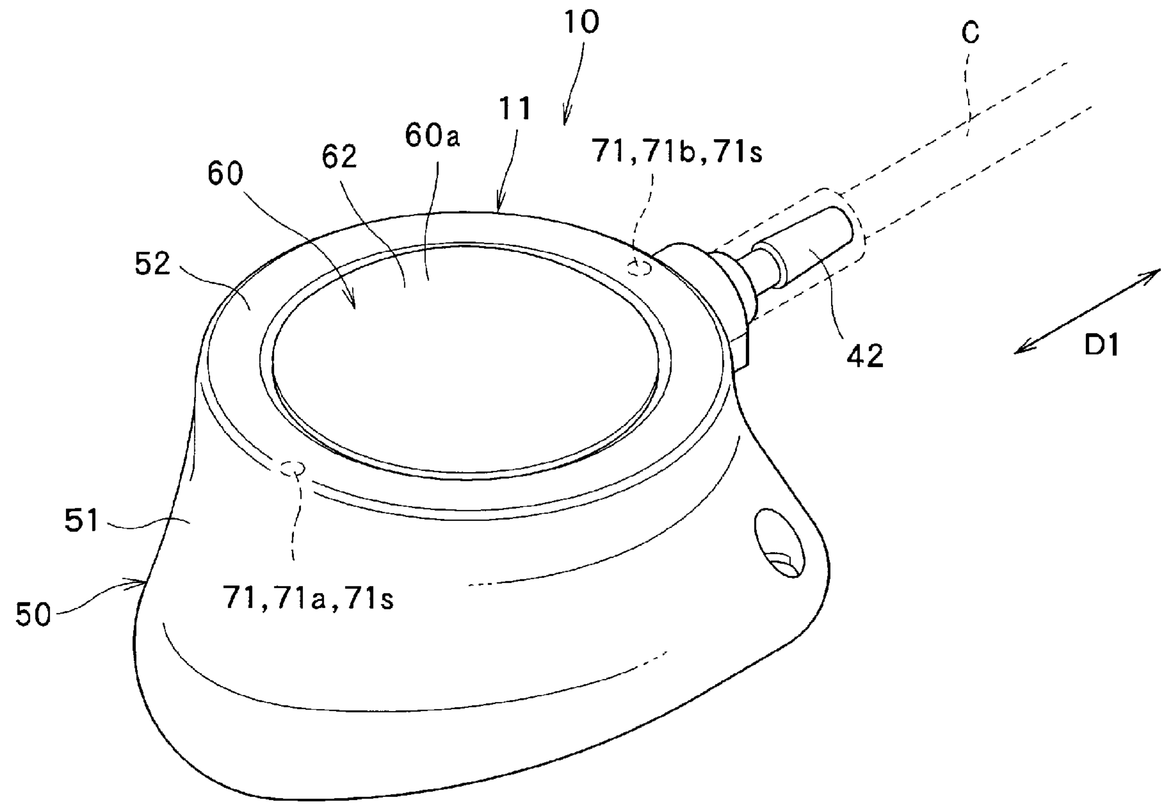
FIG. 1 is a view explaining a first example, and is a perspective view illustrating an access port.
Figure 2:
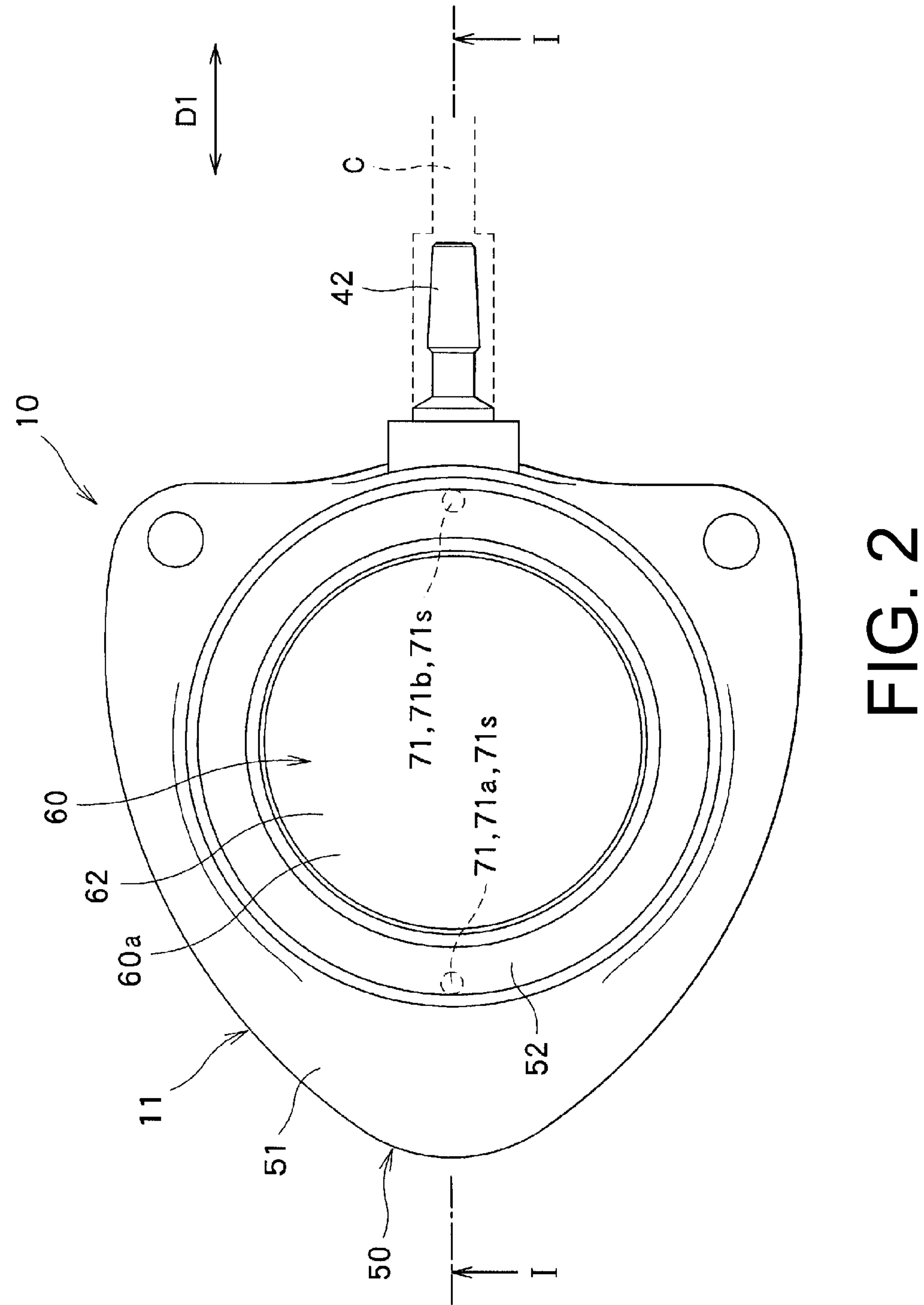
FIG. 2 is a plan view of the access port illustrated in FIG. 1 as viewed from the side of a diaphragm body.
Figure 3:
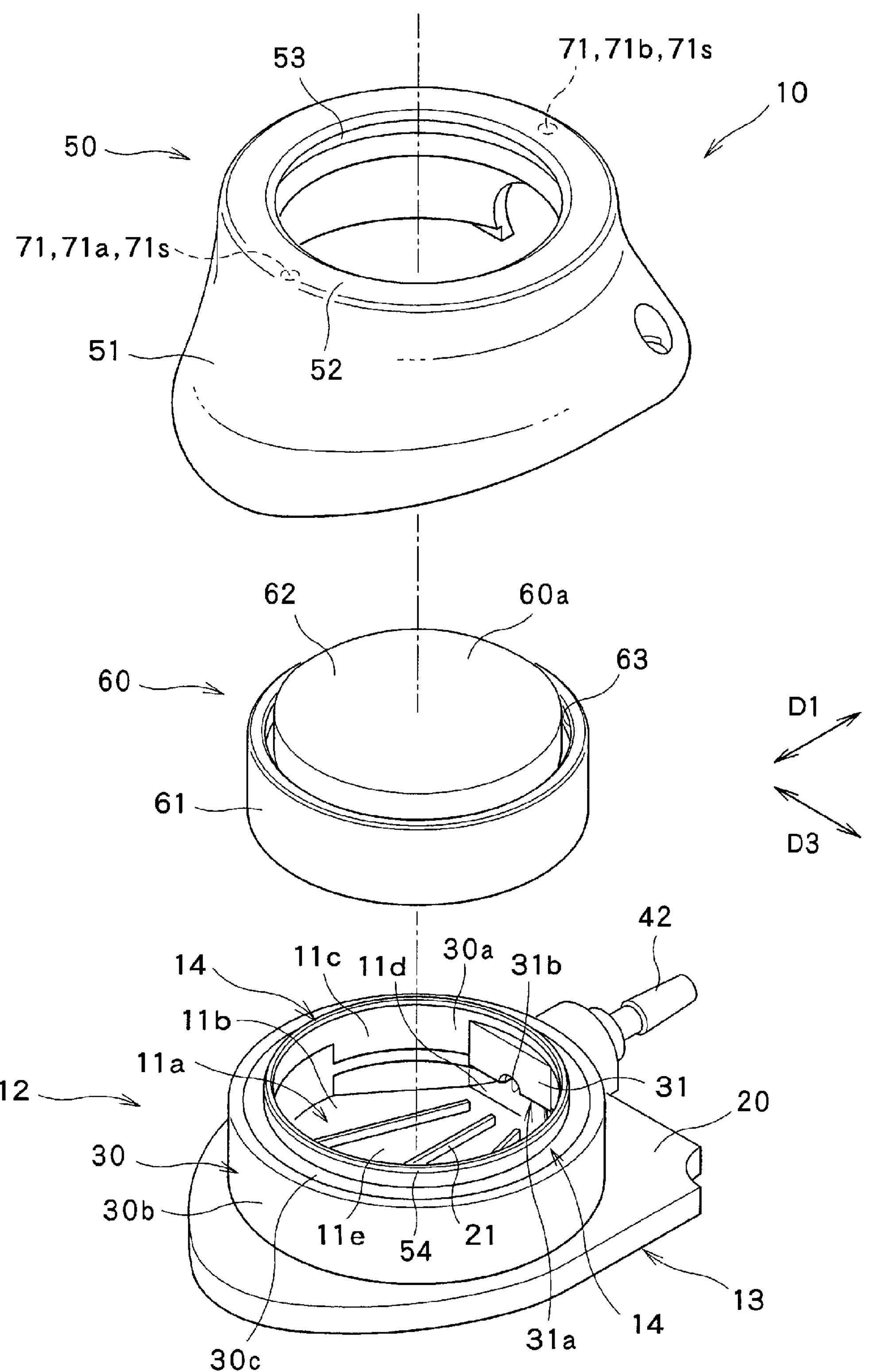
FIG. 3 is an exploded perspective view of the access port illustrated in FIG. 1.
Figure 4:
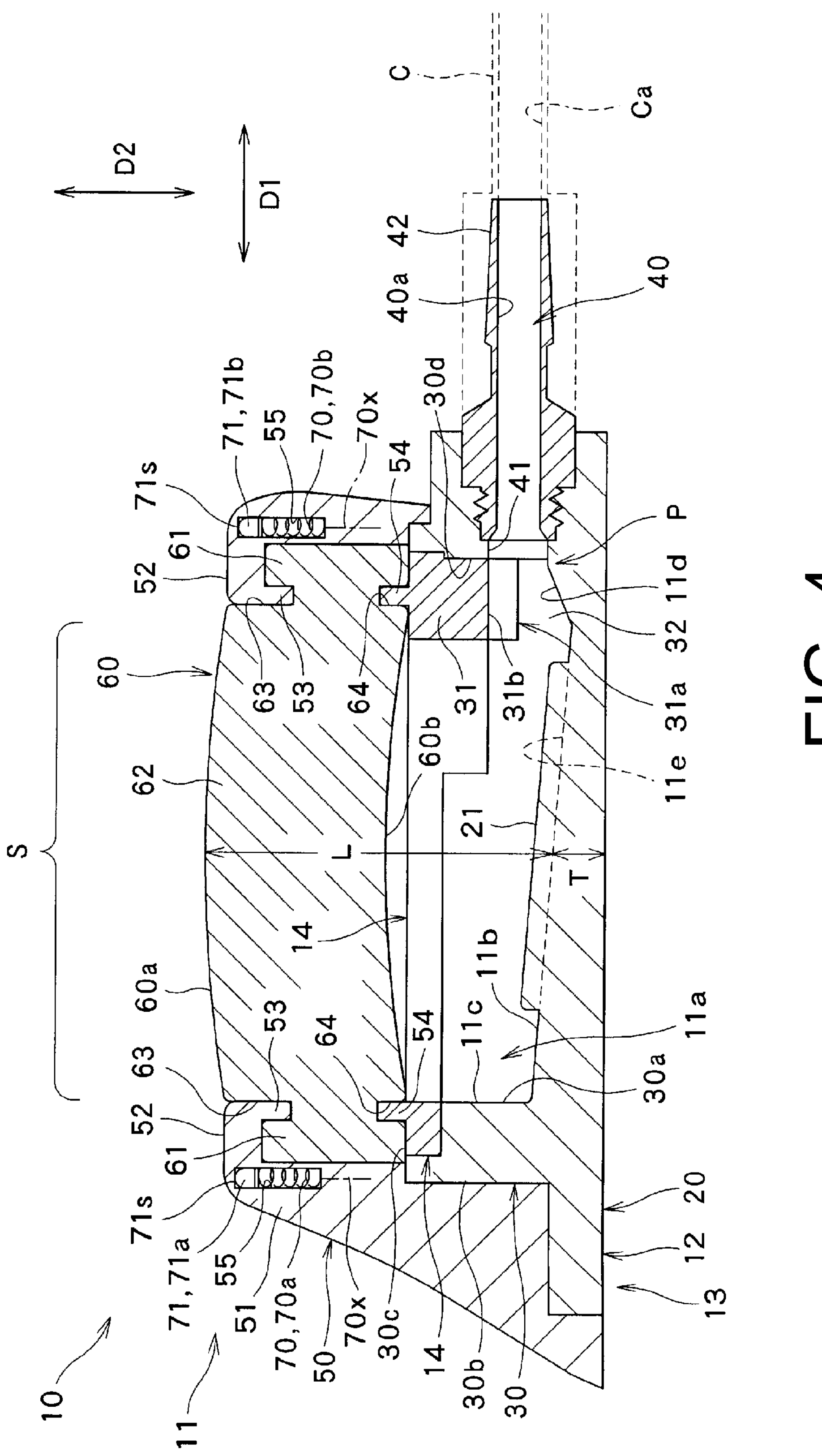
FIG. 4 is a cross-sectional view of the access port taken along line I-I in FIG. 2.
Figure 5:
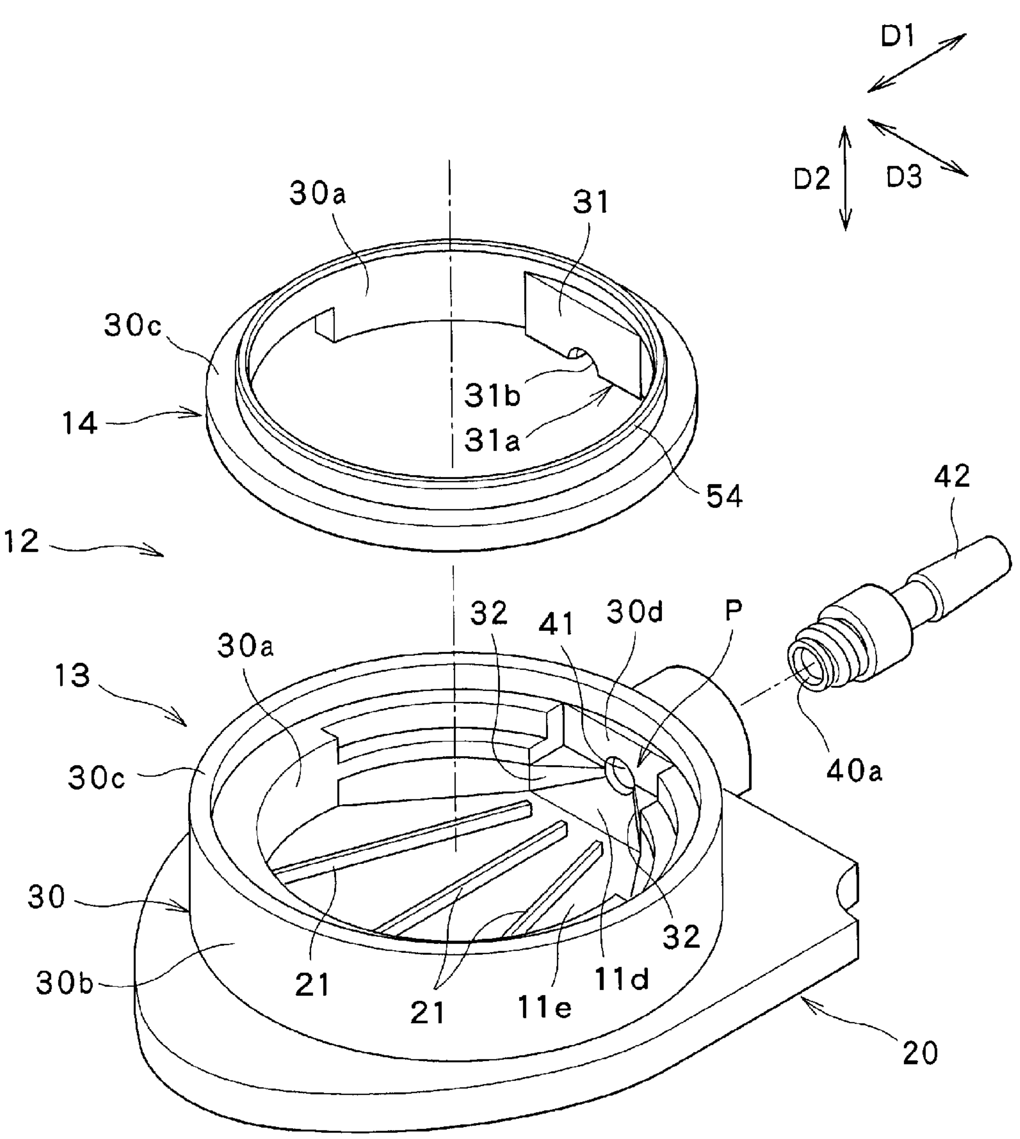
FIG. 5 is an exploded perspective view of the base member illustrated in FIG. 3.
Figure 6:
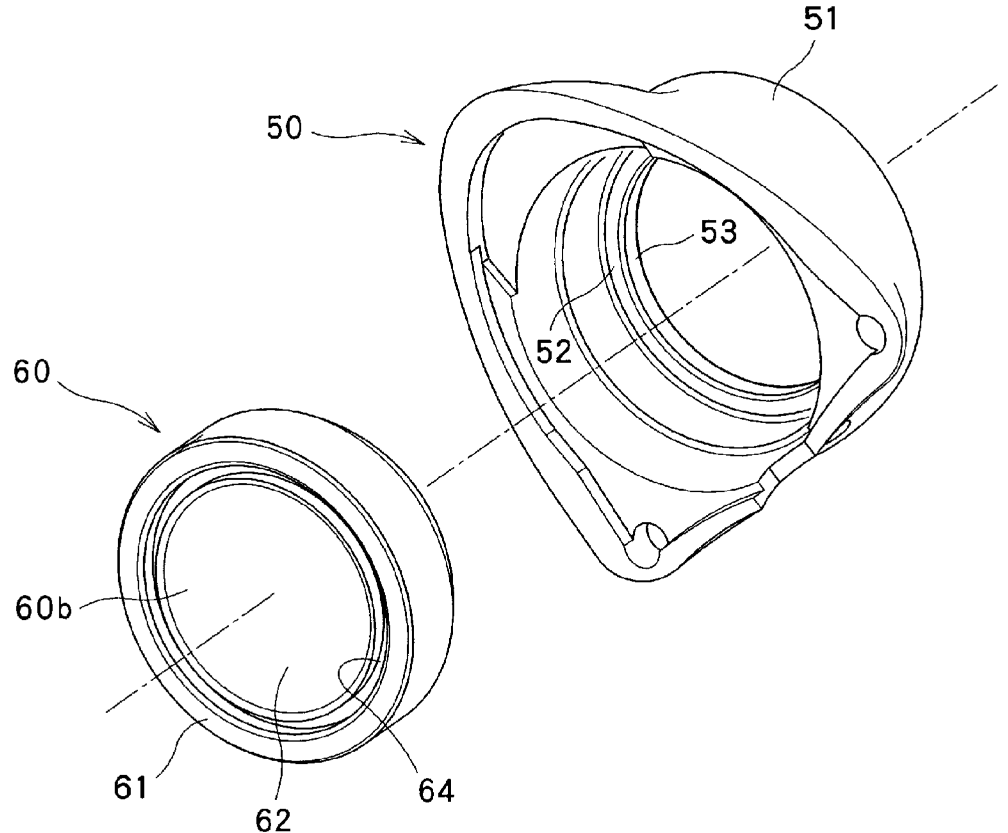
FIG. 6 is a perspective view of the diaphragm body and the lid member illustrated in FIG. 3 as viewed from the side of the other side surface of the diaphragm body.
Figure 7:
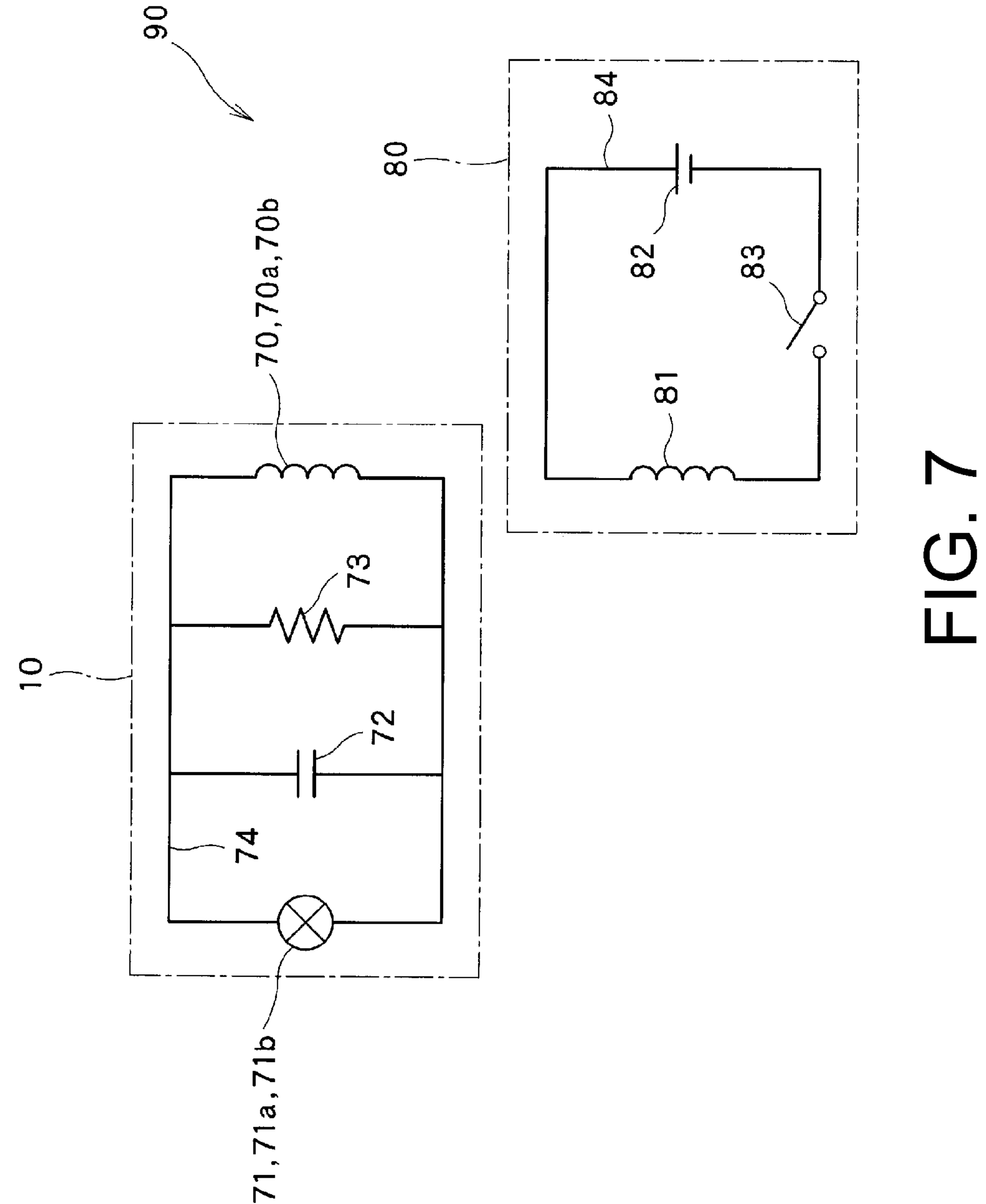
FIG. 7 is a circuit diagram illustrating a medical system including the access port illustrated in FIG. 1 and a magnetic field generation device.

FIGS. 1 to 7 are diagrams explaining an access port 10 according to a first example. Among the drawings, FIGS. 1 and 2 illustrate a perspective view and a plan view of the access port 10, respectively. FIGS. 3 and 4 illustrate an exploded perspective view and a cross-sectional view of the access port 10, respectively. FIG. 5 is an exploded perspective view of the base member 12 forming a part of the access port 10. FIG. 6 is a perspective view of the diaphragm body 60 and the lid member 50 of the access port 10. FIG. 7 is a circuit diagram illustrating a medical system 90 configured with the access port 10.

Hereinafter, the first example will be described with reference to the drawings.

Overall Configuration of Access Port

The access port 10 is used by being embedded under the skin of the patient in a state of being connected to a catheter C. As illustrated in FIGS. 1 to 4, the access port 10 includes a port body 11 including a liquid storage portion 11*a*, and a diaphragm body 60 held by the port body 11 and covering a liquid storage portion 11*a*. By inserting a dedicated puncture needle into the diaphragm body 60 and introducing a drug into the liquid storage portion 11*a*, the drug can be delivered to the vicinity of a target lesion through the catheter C.

As illustrated in FIG. 4, the port body 11 includes a base member 12 that forms (defines) the inner surface (the bottom surface 11*b* and the side surface 11*c*) of the liquid storage portion 11*a*, and a lid member 50 that is fixed to the base member 12 so that the diaphragm body 60 is held between the base member 12 and the lid member 50.

As illustrated in FIGS. 3 and 4, the base member 12 includes a bottom wall portion 20 that forms (defines) the bottom surface 11*b* of the liquid storage portion 11*a*, and a side wall portion 30 that extends from the bottom wall portion 20 to form (define) the side surface 11*c* of the liquid storage portion 11*a*. The bottom wall portion 20 is formed in a flat plate shape as a whole. The side wall portion 30 is formed in a tubular shape and is erected substantially at the center of one side surface of the bottom wall portion 20.

As illustrated in FIG. 4, the base member 12 further includes a connection passage 40 that is connected to the liquid storage portion 11*a* and allows the liquid storage portion 11*a* to communicate with the inside (lumen) Ca of the catheter C. In the illustrated example, the connection passage 40 opens to the side surface 11*c* of the base member 12. More specifically, the inner surface 40*a* of the connection passage 40 is formed (defined) by a connection passage opening 41 formed in the side wall portion 30 and the connection port 42 connected to the connection passage opening 41. The connection passage opening 41 is a through-hole extending along a direction from the inside to the outside of the annular side wall portion 30, and is open to the inner surface 30*a* and the outer surface 30*b* of the side wall portion 30. One end of the connection port 42 is inserted into the connection passage opening 41 from the side of the outer surface 30*b* of the side wall portion 30 and is fixed to the side wall portion 30. The other end of the connection port 42 is connected to one end of the catheter C. The connection passage 40 may not include the connection port 42. In this example, one end of the catheter C may be inserted into the connection passage opening 41.

The lid member 50 includes an annular lid body portion 51 that covers the side wall portion 30 of the base member 12 from the side of the outer surface 30*b*. The lid body portion 51 also covers the bottom wall portion 20 on the outer side of the side wall portion 30 from the side on which the side wall portion 30 is erected.

The lid member 50 further includes an annular lid edge portion 52 disposed to face an end surface (also "one side end surface of the side wall portion") 30*c* of the side wall portion 30 on the side opposite to the bottom wall portion 20. The annular lid edge portion 52 extends along one side end surface 30*c* of the side wall portion and toward the inside of the annular lid body portion 51 from the end portion of the lid body portion 51 on the side opposite to the bottom wall portion 20.

As illustrated in FIGS. 3, 4, and 6, the diaphragm body 60 is formed in a flat plate shape as a whole. The diaphragm body 60 is made of silicone rubber or the like. The diaphragm body 60 is disposed on one side end surface 30*c* of the side wall portion to cover the liquid storage portion 11*a*. The diaphragm body 60 has a surface (also "one side surface of the diaphragm body") 60*a* on the side opposite to the liquid storage portion 11*a* and a surface (also "other side surface of the diaphragm body") 60*b* on the side of the liquid storage portion 11*a*.

As illustrated in FIG. 4, the outer edge portion 61 of the diaphragm body 60 is held in a compressed state between one side end surface 30*c* of the side wall portion and the annular lid edge portion 52, and liquid-tightly seals the space between the base member 12 and the lid member 50. The central portion 62 of the diaphragm body 60 is arranged to face the liquid storage portion 11*a*. Since the annular lid edge portion 52 is annularly formed, the central portion 62 is exposed, and the puncture needle can be inserted into the central portion 62.

By the way, it is desired to pass a microcatheter having a smaller diameter into a catheter indwelled in the body of a patient, advance the tip of the microcatheter to a peripheral blood vessel region, and administer a drug or the like from the further vicinity of a target lesion. In this example, as a method of passing the microcatheter into the catheter, it is possible to first puncture the diaphragm body of the access port using a puncture needle, and insert the microcatheter into the lumen of the catheter through the lumen of the puncture needle, the lumen (liquid storage portion) of the access port, and the connection passage. Alternatively, it is possible to first insert a guide wire that is thinner and stiffer than the microcatheter into the lumen of the catheter through the lumen of the puncture needle, the lumen (liquid storage portion) of the access port, and the connection passage, and insert the microcatheter into the lumen of the catheter using the guide wire as a guide.

When the microcatheter or the guide wire is inserted into the lumen of the catheter, the access port and the catheter are embedded under the skin of the patient. Therefore, neither the tip of the microcatheter or the guide wire nor the connection passage can be directly observed. Therefore, the position of the connection passage is searched while rotating the tip by operating the microcatheter or the guide wire.

However, in such a method, the microcatheter and the guide wire cannot be stably and easily inserted into the connection passage.

In consideration of such circumstances, the access port of this example enables the microcatheter and the guide wire to be stably and easily inserted into the connection passage.

Inclined Region

Specifically, the following measures are taken. That is, in the cross-section along the axial direction D1 of the connection passage 40 at the connection position P where the connection passage 40 is connected to the liquid storage portion 11*a* as shown in FIG. 4, the access port 10 has an inclined region S in which the length L in the direction D2 perpendicular to the axial direction D1 between one side surface 60*a* of the diaphragm body and the inner surface of the liquid storage portion 11*a* gradually decreases as it proceeds away from the connection position P. In other words, in the inclined region S, the distance L between one side surface 60*a* of the diaphragm body and the inner surface of the liquid storage portion in the perpendicular direction D2 in the cross-section along the axial direction D1 gradually increases as it approaches the connection position P.

In such an inclined region S, the tip of the microcatheter or the guide wire inserted into the liquid storage portion 11*a* along the direction perpendicular to one side surface 60*a* of the diaphragm body is easily guided in the direction toward the connection position P (therefore, in the direction toward the connection passage 40).

The inclined region S is formed in a region exceeding half of the liquid storage portion 11*a* along the axial direction D1. As a result, even when the tip of the microcatheter or the guide wire inserted into the liquid storage portion 11*a* reaches a position deviated from the center of the liquid storage portion 11*a*, the tip of the microcatheter or the guide wire is easily guided in a direction toward the connection passage 40.

As described above, the microcatheter and the guide wire can be stably and easily inserted into the connection passage 40.

Furthermore, in the illustrated example, the inclined region S includes a half region of the liquid storage portion 11*a* on the side away from the connection position P. As a result, even when the tip of the microcatheter or the guide wire inserted into the liquid storage portion 11*a* reaches a position farther from the connection position P than the center of the liquid storage portion 11*a*, the tip is easily guided in a direction toward the connection passage 40.

In the illustrated example, in the cross-section along the axial direction D1 as shown in FIG. 4, one side surface 60*a* of the diaphragm body spreads along the axial direction D1 as a whole. On the other hand, in the cross-section along the axial direction D1 as shown in FIG. 4, the inner surface (the bottom surface 11*b*) of the liquid storage portion 11*a* in the inclined region S is inclined with respect to the axial direction D1. More specifically, the inner surface (the bottom surface 11*b*) of the liquid storage portion 11*a* in the inclined region S is inclined with respect to the axial direction D1 to be directed toward the side away from the diaphragm body 60 as it approaches the connection position P in the axial direction D1.

More specifically, as illustrated in FIG. 5, the bottom surface 11*b* of the liquid storage portion 11*a* includes a connection bottom surface 11*d* connected to the side wall surface 30*d* to which the connection passage 40 is open, and a main bottom surface 11*e* located on the side away from the connection position P with respect to the connection bottom surface 11*d* in the axial direction D1. The main bottom surface 11*e* is connected to the connection bottom surface 11*d*. The main bottom surface 11*e* is inclined with respect to the axial direction D1 toward the side away from the diaphragm body 60 as it approaches the connection position P. The inclined region S is formed by the main bottom surface 11*e*.

In the example illustrated in FIG. 4, the thickness T of the bottom wall portion 20 in the region of the main bottom surface 11*e* gradually decreases as it approaches the connection position P along the axial direction D1. As a result, the main bottom surface 11*e* is inclined with respect to the axial direction D1 toward the side away from the diaphragm body 60 as it approaches the connection position P.

Connection Bottom Surface

The access port 10 of this example is further devised so that the microcatheter and the guide wire can be more stably and easily inserted into the connection passage 40. Specifically, the following measures are taken.

That is, as illustrated in FIG. 4, the connection bottom surface 11*d* is inclined with respect to the axial direction D1 toward the side closer to the diaphragm body 60 as it approaches the connection position P. The connection bottom surface 11*d* is located on the side closer to the connection position P with respect to the main bottom surface 11*e* in the axial direction D1. With such a connection bottom surface 11*d*, the tip of the microcatheter or the guide wire guided toward the connection position P by the main bottom surface 11*e* can be guided in a direction toward the diaphragm body 60 as it further approaches the connection position P (that is, toward the connection passage opening 41 formed in the side wall portion 30). As a result, the microcatheter and the guide wire can be more stably and easily inserted into the connection passage 40.

Facing Guide Surface

Further, the access port 10 of this example is further devised so that the microcatheter and the guide wire can be stably and easily inserted into the connection passage 40. Specifically, the following measures are taken.

As illustrated in FIG. 3, the side wall portion 30 includes a protruding portion 31 provided to be spaced apart from the bottom wall portion 20. The protruding portion 31 has a facing guide surface 31*a* facing the bottom surface 11*b*. The protruding portion 31 is disposed such that the connection passage opening 41 opens at a position between the facing guide surface 31*a* and the bottom surface 11*b*. The facing guide surface 31*a* of the protruding portion 31 and the region of the bottom surface 11*b* facing the facing guide surface 31*a* can efficiently direct the tip of the microcatheter or the guide wire to the connection passage opening 41. Specifically, the movable region of the tip is limited between the facing guide surface 31*a* and the bottom surface 11*b*, and the tip is easily directed to the connection passage opening 41 open to a position between the facing guide surface 31*a* and the bottom surface 11*b*.

In particular, in the example as illustrated in FIG. 4, the facing guide surface 31*a* is disposed at a position facing the connection bottom surface 11*d*. As described above, the connection bottom surface 11*d* is inclined with respect to the axial direction D1 toward the side closer to the diaphragm body 60 (therefore, toward the side closer to the facing guide surface 31*a*) as it approaches the connection passage opening 41. Since the facing guide surface 31*a* is provided to face such a connection bottom surface 11*d*, the movable region of the tip of the microcatheter or the guide wire narrows as it approaches the connection passage opening 41, and is easily directed to the connection passage opening 41 open to a position between the facing guide surface 31*a* and the connection bottom surface 11*d*.

Further, in the example as illustrated in FIG. 3, the facing guide surface 31*a* has a concave surface 31*b* recessed away from the bottom surface 11*b* at its central portion in a width direction D3 perpendicular to both the axial direction D1 and the direction in which the facing guide surface 31*a* faces the bottom surface 11*b*. When the tip of the microcatheter or the guide wire enters the region surrounded by such a concave surface 31*b*, the movable range of the tip is limited to the region surrounded by the concave surface 31*b*. Therefore, when the region surrounded by the concave surface 31*b* and the connection passage opening 41 overlap each other when observed from the direction parallel to the axial direction D1 as shown in FIG. 4, the tip is more easily directed to the connection passage opening 41.

In the example illustrated in FIG. 4, the concave surface 31*b* is connected to a wall surface 40*a* that forms (defines) the connection passage 40. As a result, the tip of the microcatheter or the guide wire moving toward the connection passage opening 41 along the concave surface 31*b* is easily directed into the connection passage 40. That is, the possibility that the tip interferes with the side wall surface 30*d* to which the connection passage opening 41 is open to be prevented from entering the connection passage 40 is reduced.

In the example illustrated in FIG. 5, the base member 12 includes a bottom member 13 that forms the bottom surface 11*b* and a part of the side surface 11*c*, and an annular member 14 that is supported by the bottom member 13 to surround the liquid storage portion 11*a*. The annular member 14 forms another part of the side surface 11*c*. The protruding portion 31 is provided at a position of the annular member 14 corresponding to the connection position P to protrude toward the liquid storage portion 11*a*. By forming the protruding portion 31 on the annular member 14 manufactured separately from the bottom member 13, it is easy to provide the protruding portion 31 on the side wall portion 30.

The annular member 14 is made of an X-ray opaque material. As a result, even in a state where the access port 10 is embedded under the skin of the patient, it is possible to grasp the region surrounded by the annular member 14 (that is, a region where a puncture needle inserting a microcatheter or a guide wire into the liquid storage portion 11*a* is to be inserted) using the X-ray imaging technology.

Flat Wall Portion

Further, the access port 10 of this example is further devised so that the microcatheter and the guide wire can be stably and easily inserted into the connection passage. Specifically, the following measures are taken.

That is, as illustrated in FIG. 5, the side wall portion 30 includes a pair of flat wall portions 32 and 32 provided side by side in its circumferential direction. The pair of flat wall portions 32 and 32 is arranged such that the connection passage opening 41 opens to the side surface 11*c* of the liquid storage portion 11*a* at a position between the pair of flat wall portions 32 and 32. In addition, the pair of flat wall portions 32 and 32 forms tapered side surfaces extending linearly and tapered toward the connection passage opening 41 when observed from a direction parallel to a direction in which the side wall portion 30 extends from the bottom wall portion 20 (the direction D2 in the illustrated example). With such a pair of flat wall portions 32 and 32, the tip of the microcatheter or the guide wire can be efficiently directed to the connection passage 40. Specifically, due to the pair of flat wall portions 32 and 32, the movable region of the tip is narrowed as it approaches the connection passage opening 41 as well as being guided toward the connection passage opening 41.

Guide Rib

Further, the access port 10 of this example is further devised so that the microcatheter and the guide wire can be stably and easily inserted into the connection passage 40. Specifically, the following measures are taken.

That is, as illustrated in FIG. 5, the bottom wall portion 20 includes a guide rib 21 linearly extending toward the connection position P when observed from the direction (the direction D2 in the illustrated example) parallel to the direction in which the side wall portion 30 extends from the bottom wall portion 20. In the illustrated example, three guide ribs 21 radially extend from the vicinity of the connection position P. With such a guide rib 21, the tip of the microcatheter or the guide wire inserted into the liquid storage portion 11*a* can be efficiently guided toward the connection position P (therefore, toward the connection passage opening 41).

Annular Holding Groove and Annular Holding Protrusion Portion

Furthermore, the access port 10 of this example is devised to prevent the diaphragm body 60 from falling off the port body 11. Specifically, the following measures are taken.

First, as illustrated in FIGS. 3 and 4, a first annular holding groove 63 is formed in one side surface 60*a* of the diaphragm body 60. The first annular holding groove 63 is formed in the outer edge portion 61 of the diaphragm body 60. The first annular holding groove 63 extends in the direction (the direction D2 in the illustrated example) parallel to the direction in which the side wall portion 30 extends from the bottom wall portion 20 and is open to the side opposite to the liquid storage portion 11*a*. As illustrated in FIGS. 4 and 6, a first annular holding protrusion portion 53 is formed on the lid member 50 of the port body 11. The first annular holding protrusion portion 53 protrudes from the annular lid edge portion 52 in the direction parallel to the direction in which the side wall portion 30 extends from the bottom wall portion 20. As illustrated in FIG. 4, the first annular holding protrusion portion 53 extends into the first annular holding groove 63. This reduces the possibility that the diaphragm body 60 falls off the port body 11 due to the force applied to the diaphragm body 60 when the puncture needle is inserted into the diaphragm body 60 or when the puncture needle is pulled out from the diaphragm body 60.

As illustrated in FIGS. 4 and 6, a second annular holding groove 64 is formed in the other side surface 60*b* of the diaphragm body 60. The second annular holding groove 64 is formed in the outer edge portion 61 of the diaphragm body 60. The second annular holding groove 64 extends in the direction parallel to the direction in which the side wall portion 30 extends from the bottom wall portion 20 and is open to the liquid storage portion 11*a* side. As illustrated in FIGS. 3 and 4, a second annular holding protrusion portion 54 is formed on the base member 12 of the port body 11. The second annular holding protrusion portion 54 protrudes from one side end surface 30*c* of the side wall portion in the direction parallel to the direction in which the side wall portion 30 extends from the bottom wall portion 20. As illustrated in FIG. 4, the second annular holding protrusion portion 54 extends into the second annular holding groove 64. This also reduces the possibility that the diaphragm body 60 falls off the port body 11 due to the force applied to the diaphragm body 60 when the puncture needle is inserted into the diaphragm body 60 or when the puncture needle is pulled out from the diaphragm body 60.

As described above, in the illustrated example, the base member 12 includes the bottom member 13 and the annular member 14 formed separately from the bottom member 13. As illustrated in FIG. 5, the second annular holding protrusion portion 54 is formed on the annular member 14. By forming the second annular holding protrusion portion 54 in the annular member 14 separate from the bottom member 13, the shape and size of the second annular holding protrusion portion 54 can be arbitrarily changed without affecting the shape of the bottom member 13.

Metal Coil and Light Emitter

In addition, the access port 10 of this example is devised to be able to detect the position of the access port 10 embedded under the skin. Specifically, the following measures are taken.

That is, as illustrated in FIG. 4, the port body 11 has a built-in metal coil 70. The metal coil 70 is electrically connected to a light emitter 71. In the example illustrated in FIG. 7, the metal coil 70 constitutes a parallel circuit 74 together with the light emitter 71, a capacitor 72, and a resistor 73. When a magnetic field is applied to the metal coil 70 and a current flows through the circuit 74, the light emitter 71 emits light.

Since the metal coil 70 and the light emitter 71 are provided in the access port 10, when a magnetic field is applied to the vicinity of the access port 10 and a current flows through the metal coil 70, the light emitter 71 emits light. The position of the access port 10 embedded under the skin of the patient can be grasped by the light emitted by the light emitter 71. In other words, according to such an access port 10, as illustrated in FIG. 7, it is possible to construct a medical system 90 capable of detecting the position of the access port 10 embedded under the skin together with a magnetic field generation device 80 that generates a magnetic field.

In addition, since the access port 10 includes the metal coil 70, the position of the access port 10 embedded under the skin of the patient can also be grasped using the X-ray imaging technology.

In the illustrated example, the metal coil 70 and the light emitter 71 are embedded in the lid member 50. As a result, light emitted from the light emitter 71 easily reaches the outside of the access port 10. In addition, in the illustrated example, the metal coil 70 and the light emitter 71 are entirely embedded in the lid member 50, and they have no portion exposed to the surface of the lid member 50. As a result, the metal coil 70 and the light emitter 71 are prevented from coming into contact with the body fluid of the patient in which the access port 10 is embedded, and the drug or the like stored in the liquid storage portion 11*a*. In the illustrated example, the lid member 50 has translucency. Thus, the light emitted from the light emitter 71 in the lid member 50 can be delivered to the outside of the lid member 50 (the access port 10). A light emitting surface 71*s* of the light emitter 71 is preferably disposed as close as possible to the outer surface of the lid member 50 (the access port 10). As the light emitting surface 71*s* is closer to the outer surface, the light emitted from the light emitter 71 easily reaches the outside of the access port 10. Therefore, it is easy to deliver the light emitted from the light emitter 71 to the skin surface of the patient in a state where the access port 10 is embedded under the skin of the patient. That is, the light emitted from the light emitter 71 is easily perceived by the person around the patient.

In the illustrated example, the port body 11 includes two metal coils 70*a* and 70*b* and at least two light emitters 71*a* and 71*b* electrically connected to the metal coils 70*a* and 70*b*, respectively. One metal coil 70*a* and the light emitter 71*a* electrically connected to the metal coil 70*a*, and the other metal coil 70*b* and the light emitter 71*b* connected to the metal coil 70*b* are provided at positions around the liquid storage portion 11*a* to be separated from each other. One side surface 60*a* of the diaphragm body is exposed to a region between two sets of the metal coils 70*a* and 70*b* and the light emitters 71*a* and 71*b*. Therefore, even in a state where the access port 10 is embedded under the skin of the patient, if a magnetic field is applied to the vicinity of the access port 10 to cause the light emitters 71*a* and 71*b* to emit light, the position of the exposed one side surface 60*a* of the diaphragm body (that is, a region into which a puncture needle inserting a microcatheter or a guide wire into the liquid storage portion 11*a* is to be inserted) can be grasped.

In the illustrated example, the axis 70*x* of each metal coil 70 extends in a direction parallel to the direction in which the side wall portion 30 extends from the bottom wall portion 20 (the direction D2 in the illustrated example). As understood from FIG. 4, the base member 12 and the lid member 50 constituting the port body 11 have portions such as the side wall portion 30 and the lid body portion 51, extending along the direction in which the side wall portion 30 extends from the bottom wall portion 20. Therefore, when the extension direction of the axis 70*x* is along the direction in which the side wall portion 30 extends from the bottom wall portion 20, it is possible to suppress an increase in the size of the port body 11 due to the incorporation of the metal coil 70 in the port body 11. Further, in the illustrated example, the light emitter 71 is disposed on the axis 70*x* of each metal coil 70. By disposing the light emitter 71 in this manner, it is possible to suppress an increase in the size of the port body 11 due to the incorporation of the metal coil 70 and the light emitter 71 in the port body 11. In addition, when observed from the direction in which the side wall portion 30 extends from the bottom wall portion 20, the light emitter 71 can be disposed in the vicinity of the diaphragm body 60. As a result, the position of the diaphragm body 60 can be grasped more accurately.

In the illustrated example, the circuit 74 including the metal coil 70 and the light emitter 71 is disposed in a housing chamber 55 provided in the lid body portion 51 of the lid member 50. The capacitor 72 and the resistor 73 are disposed in a space surrounded by the metal coil 70. As a result, the circuit 74 can be compactly housed in the housing chamber 55.

Any device can be employed as the magnetic field generation device 80. For example, the magnetic field generation device 80 may be a device including a circuit 84 in which a metal coil 81, a power supply 82, and a switch 83 are electrically connected in series as illustrated in FIG. 7. According to such a magnetic field generation device 80, a magnetic field can be generated in the metal coil 81 by closing the switch 83.

Next, a second example of an access port will be described with reference to FIGS. 8 to 13.

Figure 8:
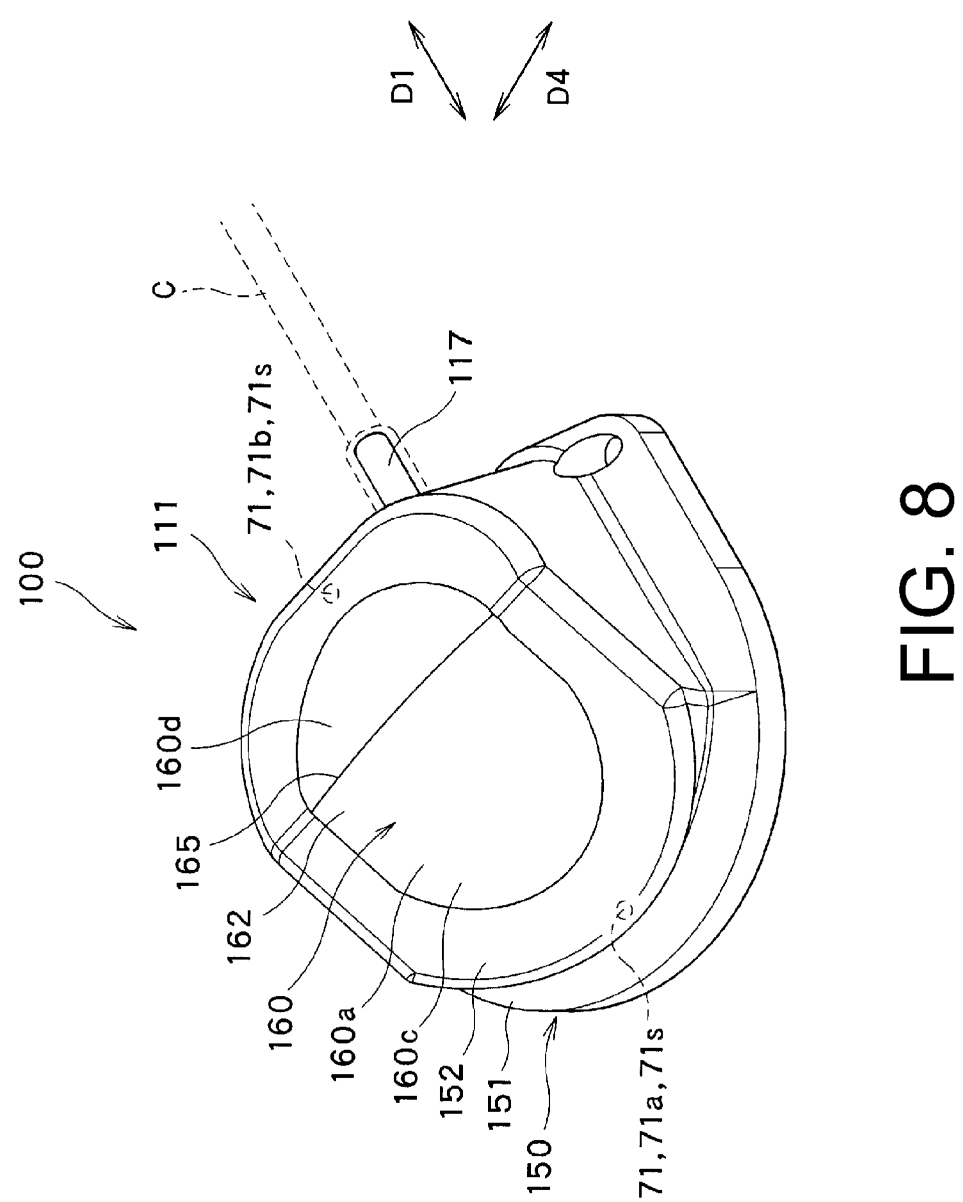
FIG. 8 is a view explaining a second example, and is a perspective view illustrating an access port.
Figure 9:
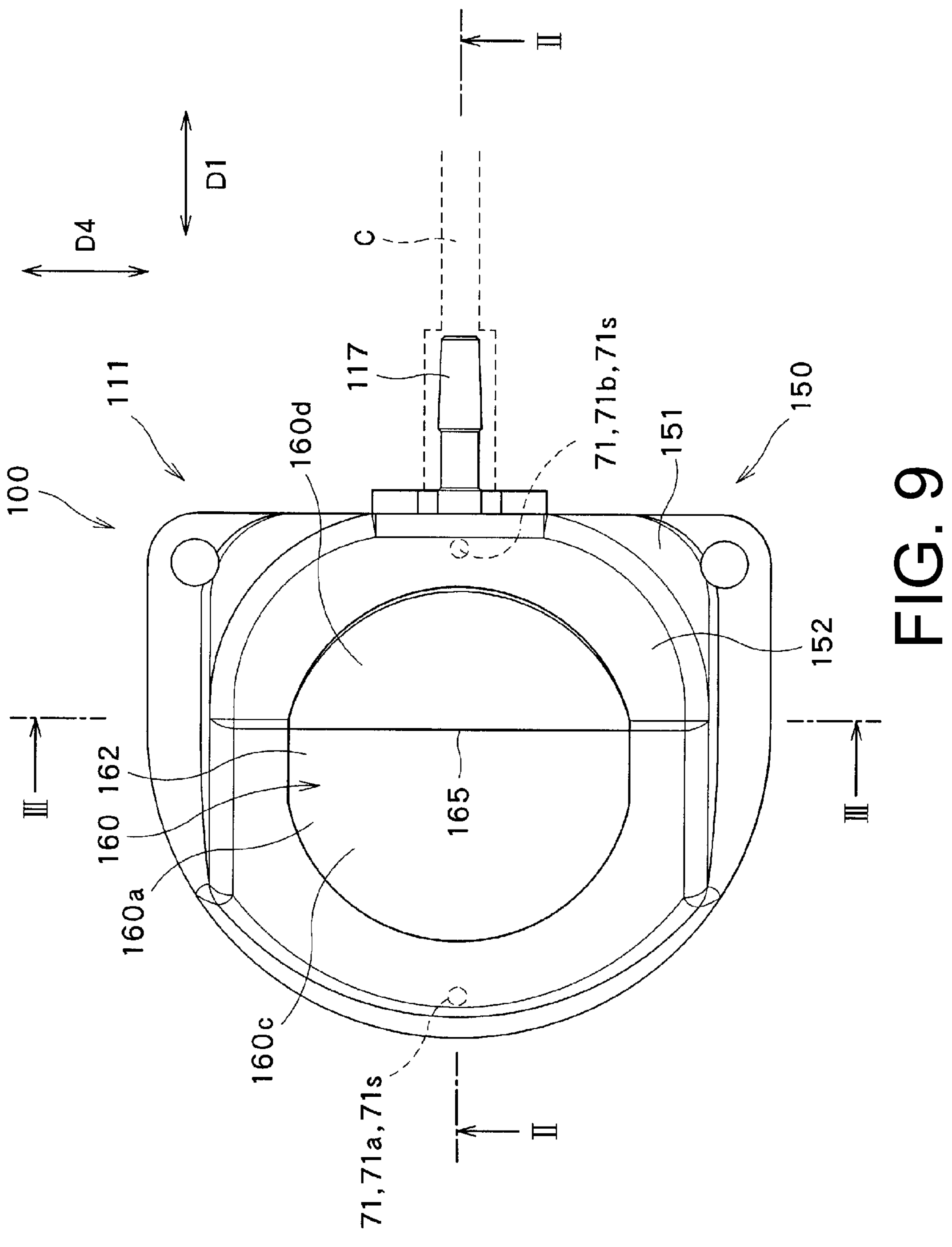
FIG. 9 is a plan view of the access port illustrated in FIG. 8 as viewed from the side of the diaphragm body.
Figure 10:
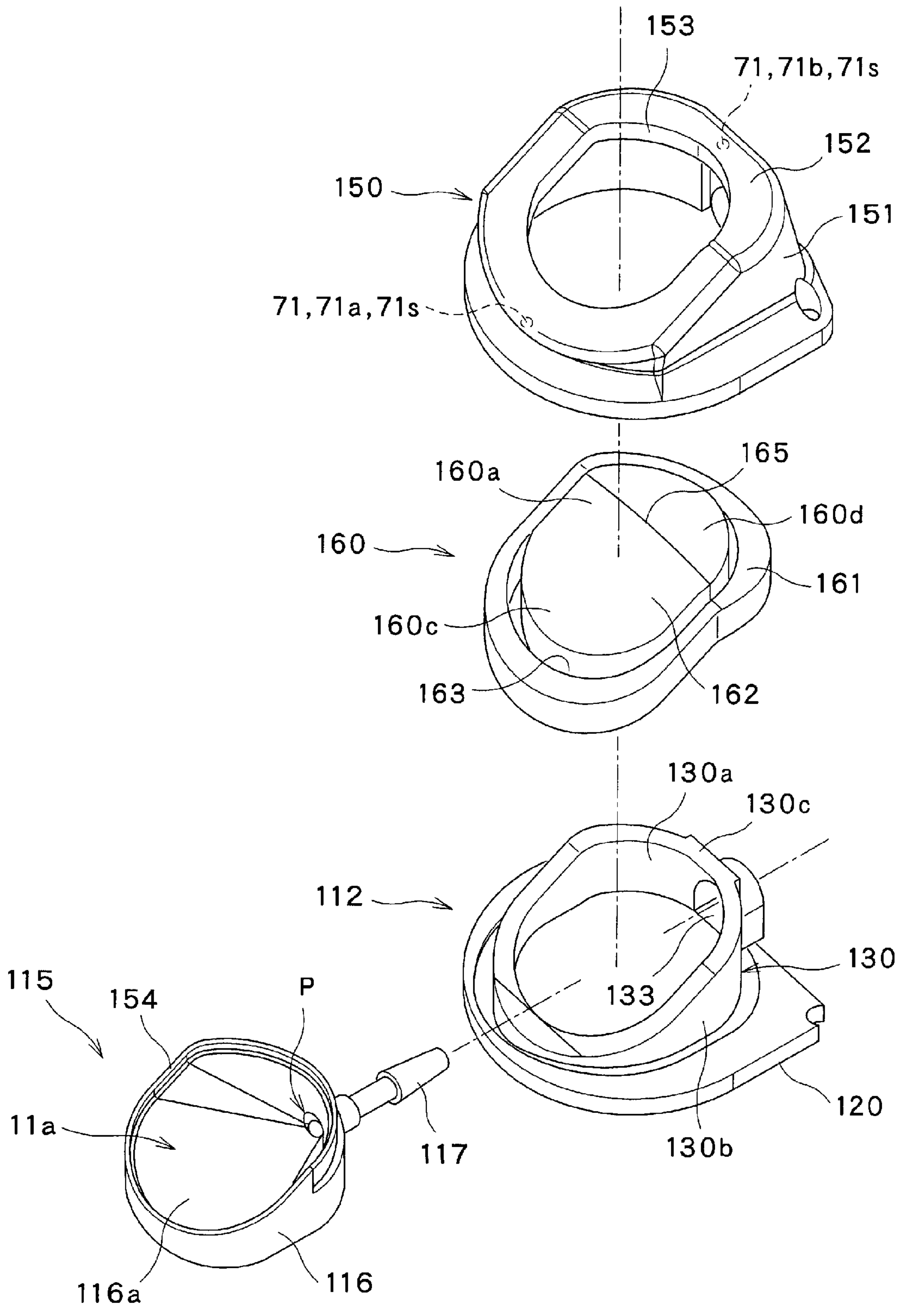
FIG. 10 is an exploded perspective view of the access port illustrated in FIG. 8.
Figure 11:
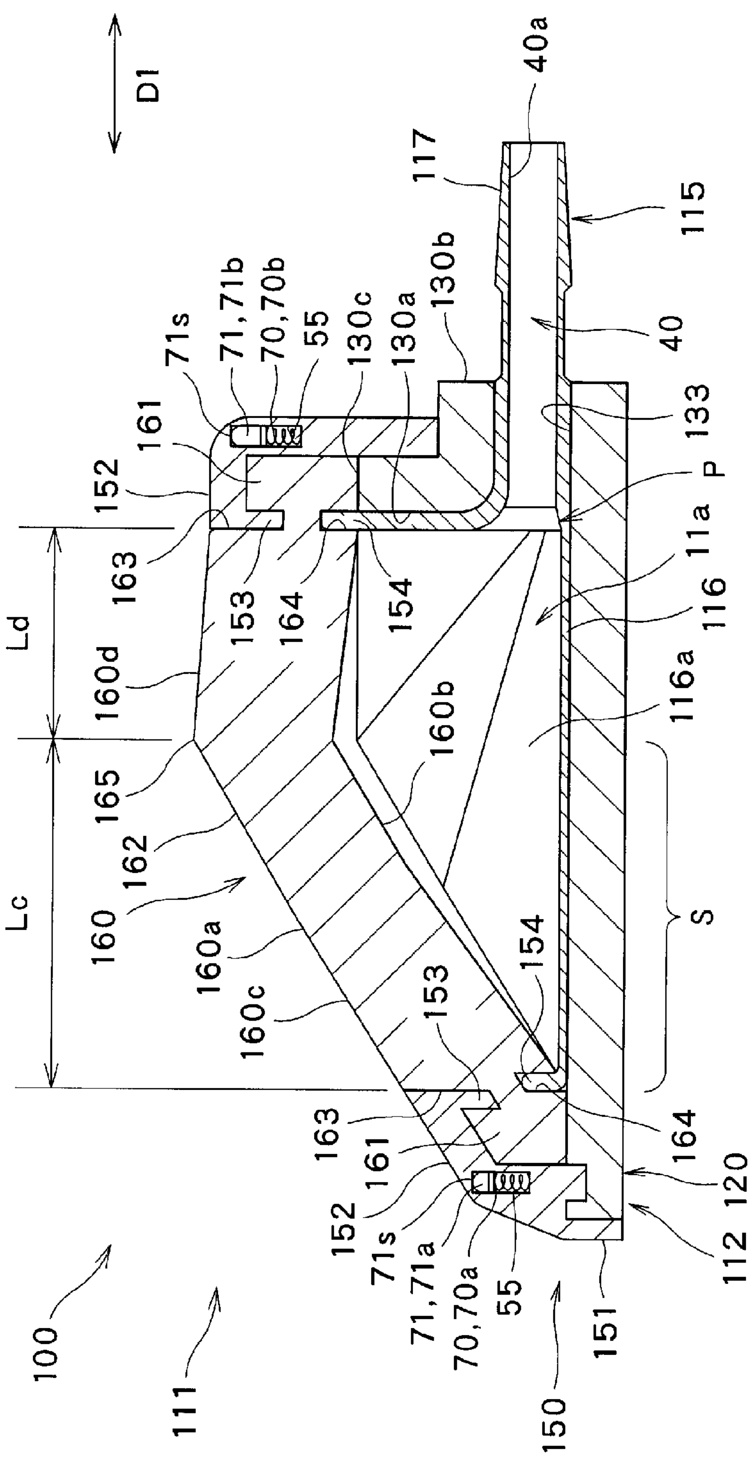
FIG. 11 is a cross-sectional view of the access port taken along line II-II of FIG. 9.
Figure 12:
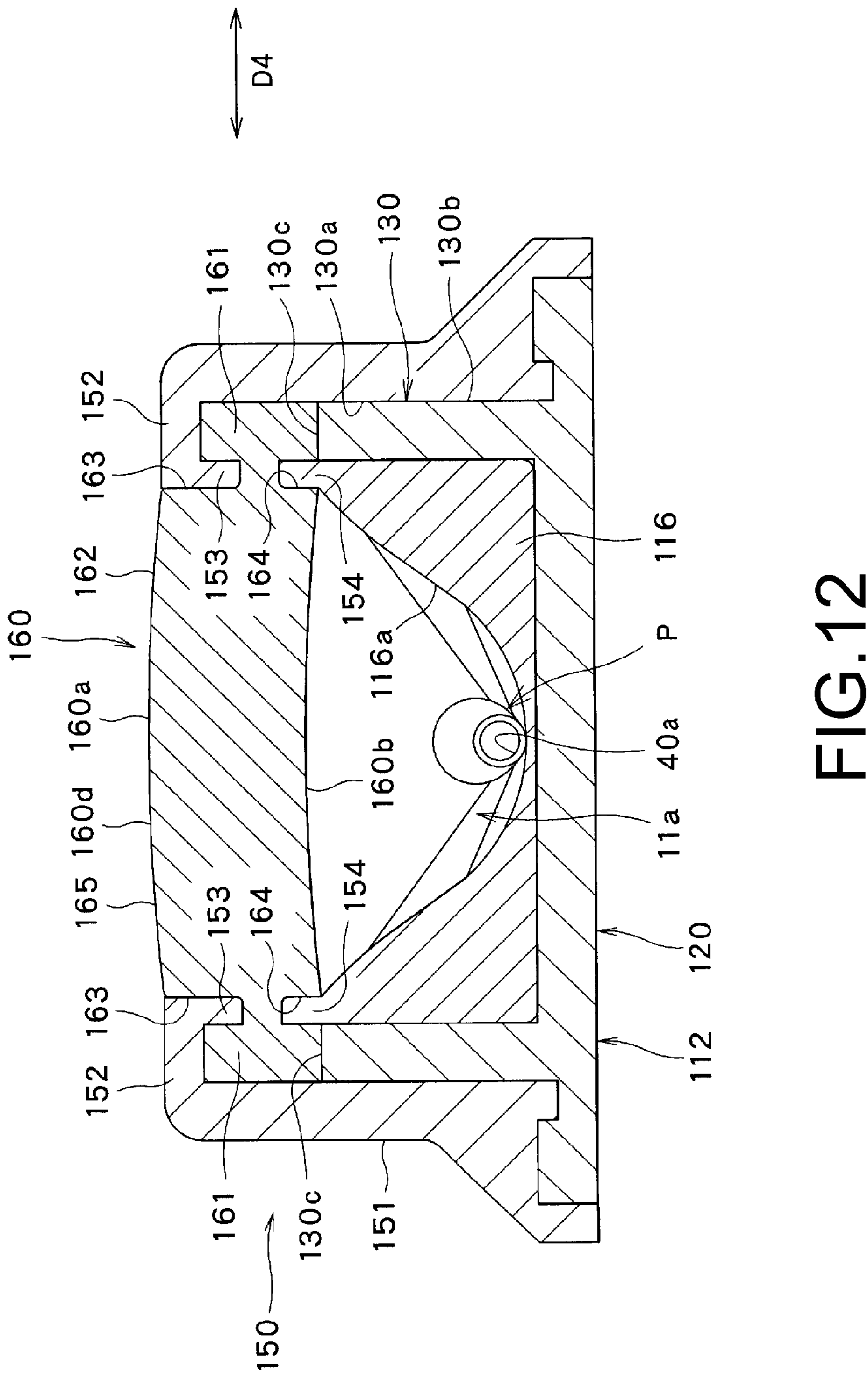
FIG. 12 is a cross-sectional view of the access port taken along line of FIG. 9.
Figure 13:
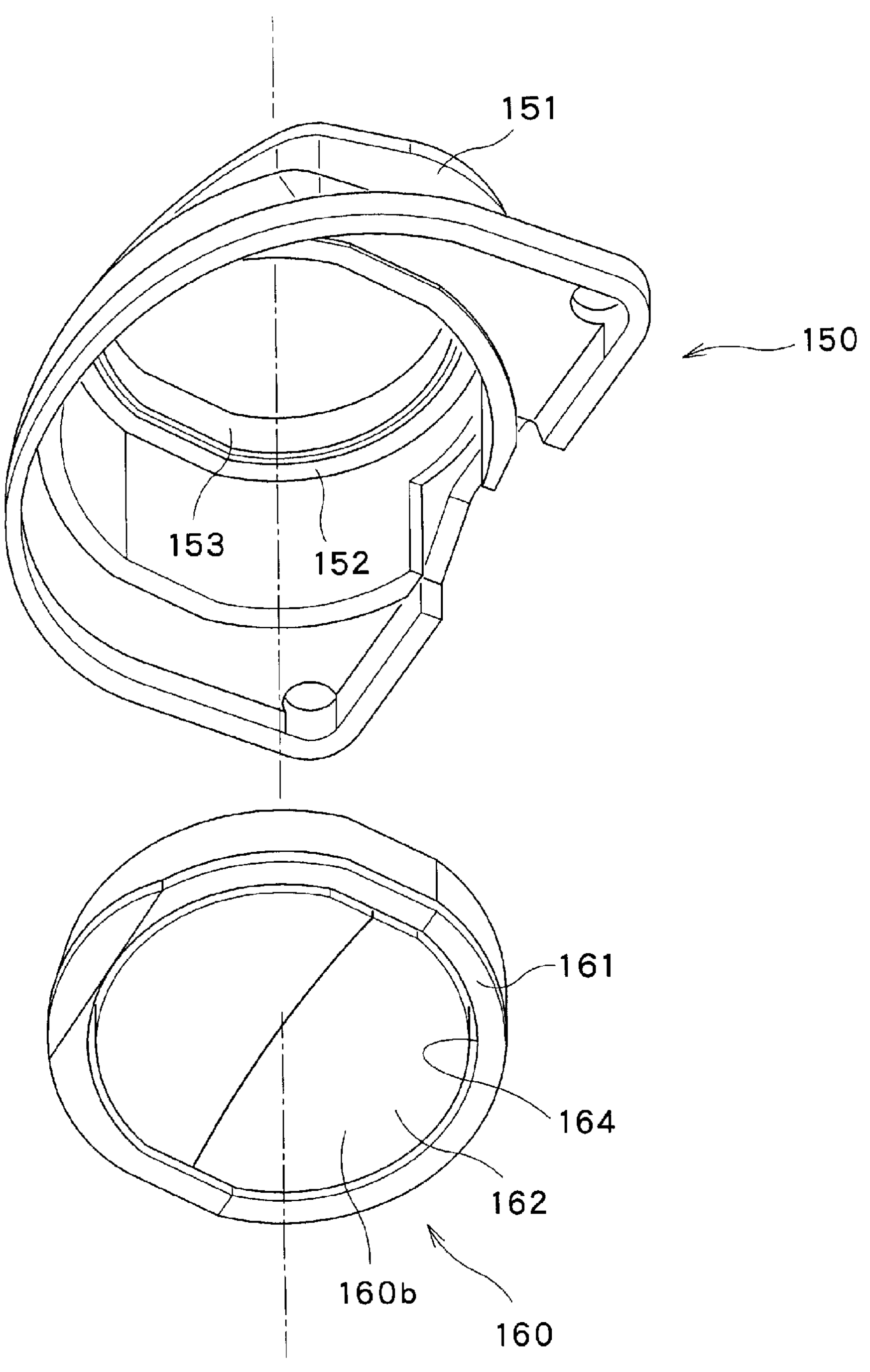
FIG. 13 is a perspective view of the diaphragm body and the lid member illustrated in FIG. 10 as viewed from the side of the other side surface of the diaphragm body.

FIGS. 8 to 13 are diagrams describing an access port 100 according to the second example. Among the drawings, FIGS. 8 and 9 illustrate a perspective view and a plan view of the access port 100, respectively. FIG. 10 illustrates an exploded perspective view of the access port 100, and FIGS. 11 and 12 illustrate cross-sectional views of the access port 100. FIG. 13 is a perspective view of a diaphragm body 160 and a lid member 150 of the access port 100.

The second example illustrated in FIGS. 8 to 13 is different in that, in a cross-section along the axial direction D1 of the connection passage 40 as shown in FIG. 11, while a bottom surface of the liquid storage portion 11*a* extends in parallel to the axial direction D1, a surface (one side surface of the diaphragm body) 160*a* of the diaphragm body 160 on the side opposite to the liquid storage portion 11*a* is inclined with respect to the axial direction D1. In addition, the access port 100 includes a surface layer member 115 forming the inner surface of the liquid storage portion 11*a* and the connection passage 40. However, other configurations are substantially the same as those of the first example illustrated in FIGS. 1 to 7. In the second example illustrated in FIGS. 8 to 13, the same parts as those of the first example illustrated in FIGS. 1 to 7 are denoted by the same reference numerals, and detailed description thereof is omitted.

The access port 100 according to the second example will be described in more detail below with reference to FIGS. 8 to 13.

Overall Configuration of Access Port

As illustrated in FIGS. 10 to 12, the access port 100 includes a port body 111 including a liquid storage portion 11*a*, and a diaphragm body 160 held by the port body 111 and covering the liquid storage portion 11*a*.

The port body 111 includes a base member 112, a surface layer member 115 that is supported by the base member 112 and forms (defines) an inner surface of the liquid storage portion 11*a*, and a lid member 150 that is fixed to the base member 112 and holds the diaphragm body 160 between the base member 112 and the surface layer member 115.

As illustrated in FIG. 10, the base member 112 includes a bottom wall portion 120 having a flat plate shape as a whole and a side wall portion 130 extending from the bottom wall portion 120. The side wall portion 130 is formed in a tubular shape as a whole, and is erected substantially at the center of one side surface of the bottom wall portion 120. The side wall portion 130 has a through-hole 133 through which a connection port 117 of the surface layer member 115 described later is inserted. The through-hole 133 extends along a direction from the inside to the outside of the annular side wall portion 130 and is open to the inner surface 130*a* and the outer surface 130*b* of the side wall portion 130.

On the side of the side wall portion 130 away from the through-hole 133 in the axial direction D1, an end surface (one side end surface of the side wall portion) 130*c* on the side opposite to the bottom wall portion 20 is inclined toward the side closer to the bottom wall portion 120 as it proceeds away from the through-hole 133 in the axial direction D1.

As illustrated in FIGS. 10 to 12, the lid member 150 includes an annular lid body portion 151 that covers the side wall portion 130 of the base member 112 from the side of the outer surface 130*b*. The lid body portion 151 covers the bottom wall portion 120 on the outer side of the side wall portion 130 from the side on which the side wall portion 130 is erected.

The lid member 150 further includes an annular lid edge portion 152 disposed to face one side end surface 130*c* of the side wall portion. The annular lid edge portion 152 extends along one side end surface 130*c* of the side wall portion toward the inner side of the annular lid body portion 151 from the end portion of the lid body portion 151 on the side opposite to the bottom wall portion 120.

The diaphragm body 160 is formed in a plate shape as a whole. The diaphragm body 160 is made of silicone rubber or the like. The diaphragm body 160 is disposed on one side end surface 130*c* of the side wall portion to cover the liquid storage portion 11*a*. The diaphragm body 160 has a surface (one side surface of the diaphragm body) 160*a* on the side opposite to the liquid storage portion 11*a* and a surface (other side surface of the diaphragm body) 160*b* on the side of the liquid storage portion 11*a*.

The outer edge portion 161 of the diaphragm body 160 is held in a compressed state between one side end surface 130*c* of the side wall portion and the annular lid edge portion 152, and liquid-tightly seals the space between the base member 112 and the lid member 150. The central portion 162 of the diaphragm body 160 is arranged to face the liquid storage portion 11*a*. Since the annular lid edge portion 152 is annularly formed, the central portion 162 is exposed, and the puncture needle can be inserted into the central portion 162.

As illustrated in FIG. 10, the surface layer member 115 includes a surface layer member body portion 116 that covers the inner surfaces of the bottom wall portion 120 and the side wall portion 130 and forms the inner surface of the liquid storage portion 11*a*, and a connection port 117 that is connected to the surface layer member body portion 116 and forms the connection passage 40. One end of the connection port 117 is connected to the surface layer member body portion 116. The connection port 117 is open to the liquid storage portion 11*a* at the connection position P on the inner surface 116a of the surface layer member body portion 116. As illustrated in FIG. 11, the connection port 117 is inserted into the through-hole 133 provided in the side wall portion 130. The other end of the connection port 117 is disposed outside the side wall portion 130. The other end of the connection port 117 is connected to one end of the catheter C.

In the illustrated example, the inner surface 116*a* of the surface layer member body portion 116 extends in parallel to the axial direction D1 in the cross-section along the axial direction D1 as shown in FIG. 11.

Diaphragm Body

The access port 100 of this example also enables the microcatheter and the guide wire to be stably and easily inserted into the connection passage. Specifically, the following measures are taken.

As illustrated in FIGS. 9 and 11, the diaphragm body 160 has a bent portion 165 extending along a direction (in the illustrated example, a direction D4 to be described later) perpendicular to the cross-section along the axial direction D1 of the connection passage 40. In the central portion 162 of the diaphragm body 160, one side surface 160*a* of the diaphragm body has a first surface 160*c* located on one side of the bent portion 165 in the axial direction D1, and a second surface 160*d* located on the other side of the bent portion 165 in the axial direction D1 and inclined with respect to the first surface 160*c*. The first surface 160*c* is located on the side away from the connection position P in the axial direction D1. On the other hand, the second surface 160*d* is located on the side closer to the connection position P in the axial direction D1 with respect to the first surface 160*c*.

The first surface 160*c* is inclined with respect to the axial direction D1. The first surface 160*c* is inclined with respect to the axial direction D1 toward the side away from the inner surface of the liquid storage portion 11*a* as it approaches the connection position P in the axial direction D1.

As described above, in the cross-section of the access port 100 along the axial direction D1 as shown in FIG. 11, the inner surface 116*a* of the surface layer member body portion 116 extends in parallel to the axial direction D1. On the other hand, in the cross-section along the axial direction D1, the first surface 160*c* which is a part of one side surface 160*a* of the diaphragm body is inclined with respect to the axial direction D1. The inclined region S is formed in the access port 100 by the inner surface 116*a* and the first surface 160*c*. In such an inclined region S, the tip of the microcatheter or the guide wire inserted into the liquid storage portion 11*a* along the direction perpendicular to one side surface 160*a* of the diaphragm body is easily guided in the direction toward the connection position P (therefore, in the direction toward the connection passage 40).

In the illustrated example, the inclination angle of the second surface 160*d* with respect to the axial direction D1 is smaller than the inclination angle of the first surface 160*c* with respect to the axial direction D1. As a result, even when the access port 100 is embedded under the skin of the patient, the position of the first surface 160*c* can be grasped.

A length Ld of the second surface 160*d* along the axial direction D1 is shorter than a length Lc of the first surface 160*c* along the axial direction D1. Thus, the first surface 160*c* (a region into which a puncture needle inserting a microcatheter or a guide wire into the liquid storage portion 11*a* is to be inserted) can be widely secured.

Surface Layer Member

The access port 100 of this example is further devised so that the microcatheter and the guide wire can be stably and easily inserted into the connection passage. Specifically, the following measures are taken.

That is, as illustrated in FIG. 11, the inner surface 116*a* of the surface layer member body portion 116 (the inner surface of the liquid storage portion 11*a*) and the inner surface of the connection port 117 (the wall surface 40*a* forming the connection passage 40) are connected seamlessly. In other words, the surface layer member 115 connects the inner surface of the liquid storage portion 11*a* and the connection passage 40 seamlessly. This reduces the possibility that the tip of the microcatheter or the guide wire interferes with the inner surface 116*a* of the surface layer member body portion 116 or the connection port 117 and is prevented from entering the connection passage 40.

The inner surface 116*a* of the surface layer member body portion 116 has a funnel shape. As illustrated in FIG. 12, in the cross-section perpendicular to the axial direction D1 of the connection passage 40, the inner surface 116*a* of the surface layer member body portion 116 is inclined with respect to the other side surface 160*b* of the diaphragm body to approach the diaphragm body 160 on both outer sides in the direction D4 along the other side surface 160*b* of the diaphragm body. In other words, in the cross-section perpendicular to the axial direction D1 of the connection passage 40, the inner surface 116*a* of the surface layer member body portion 116 extends in a U-shape. The inner surface 116*a* of the surface layer member body portion 116 allows the movable region of the tip of the microcatheter or the guide wire to be narrowed in the direction D4, and the tip is easily directed to the connection position P.

In the illustrated example, the surface layer member 115 is made of metal. As a result, even in a state where the access port 100 is embedded under the skin of the patient, the position (that is, a region into which a puncture needle inserting a microcatheter or a guide wire into the liquid storage portion 11*a* is to be inserted) of the liquid storage portion 11*a* formed by the surface layer member body portion 116 and the position (that is, the connection position P) of the connection port 117 can be grasped using the X-ray imaging technology.

Annular Holding Groove and Annular Holding Protrusion Portion

Furthermore, the access port 100 of this example is also devised to prevent the diaphragm body 160 from falling off the port body 111. Specifically, the following measures are taken.

First, as illustrated in FIGS. 10 to 12, a first annular holding groove 163 is formed in one side surface 160*a* of the diaphragm body 160. The first annular holding groove 163 is formed in the outer edge portion 161 of the diaphragm body 160. The first annular holding groove 163 extends in a direction parallel to the direction in which the side wall portion 130 extends from the bottom wall portion 120 of the base member 112 and is open to the side opposite to the liquid storage portion 11*a*. As illustrated in FIGS. 11 to 13, a first annular holding protrusion portion 153 is formed on the lid member 150 of the port body 111. The first annular holding protrusion portion 153 protrudes from the annular lid edge portion 152 in the direction parallel to the direction in which the side wall portion 130 extends from the bottom wall portion 120. As illustrated in FIGS. 11 and 12, the first annular holding protrusion portion 153 extends into the first annular holding groove 163. This reduces the possibility that the diaphragm body 160 falls off the port body 111 due to the force applied to the diaphragm body 160 when the puncture needle is inserted into the diaphragm body 160 or when the puncture needle is pulled out from the diaphragm body 160.

As illustrated in FIGS. 11 to 13, a second annular holding groove 164 is formed in the other side surface 160*b* of the diaphragm body 160. The second annular holding groove 164 is formed in the outer edge portion 161 of the diaphragm body 160. The second annular holding groove 164 extends in the direction parallel to the direction in which the side wall portion 130 extends from the bottom wall portion 120 of the base member 112 and is open to the liquid storage portion 11*a* side. As illustrated in FIGS. 10 to 12, the edge portion of the surface layer member body portion 116 forms a second annular holding protrusion portion 154 extending in the direction parallel to the direction in which the side wall portion 130 extends from the bottom wall portion 120. As illustrated in FIGS. 11 and 12, the second annular holding protrusion portion 154 extends into the second annular holding groove 164. This also reduces the possibility that the diaphragm body 160 falls off the port body 111 due to the force applied to the diaphragm body 160 when the puncture needle is inserted into the diaphragm body 160 or when the puncture needle is pulled out from the diaphragm body 160.

Although the access ports 10 and 100 according to the first and second examples have been described above with reference to FIGS. 1 to 13, the configuration of the access port 10 or 100 is not limited to that described above. Various changes can be made to the configuration of the access port illustrated in FIGS. 1 to 13.

For example, in the access port 100 according to the second example, the diaphragm body 160 may not have the bent portion 165. In other words, one side surface 160*a* of the diaphragm body may not have the second surface 160*d* inclined with respect to the first surface 160*c*.

In addition, the access ports 10 and 100 according to the first and second examples may not include the light emitter 71. In this instance, the magnetic field generation device 80 may have a notification function of detecting and notifying of the disturbance of the magnetic field by the metal coil 70 of the access port 10 or 100 when the magnetic field is applied by the magnetic field generation device 80. In this way, it is possible to grasp that the metal coil 70 exists in the vicinity of the magnetic field generation device 80 (the presence of the diaphragm body 60 or 160 of the access port 10 or 100) by the notification function of the magnetic field generation device 80.

In addition, the access ports 10 and 100 according to the first and second examples may include three or more metal coils 70 or three or more sets of metal coils 70 and light emitters 71. If three or more metal coils 70 or three or more sets of metal coils 70 and light emitters 71 are provided at positions around the liquid storage portion 11*a* to be separated from each other, the position of the liquid storage portion 11*a* (a region where a puncture needle inserting a microcatheter or a guide wire into the liquid storage portion 11*a* is to be inserted) can be more easily grasped.

Figure 14:
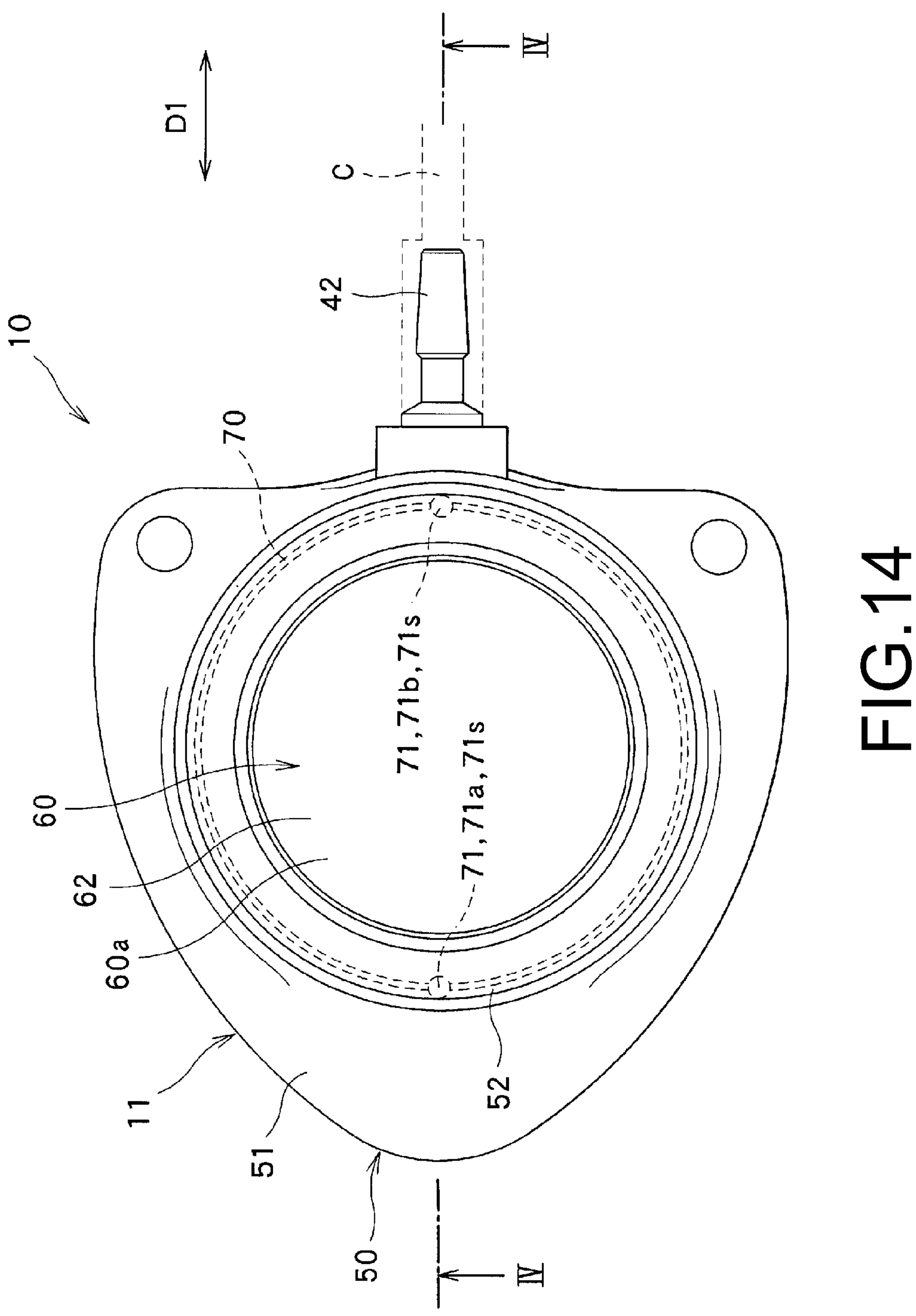
FIG. 14 is a view corresponding to FIG. 2, and is a plan view explaining a modification of the access port.
Figure 15:
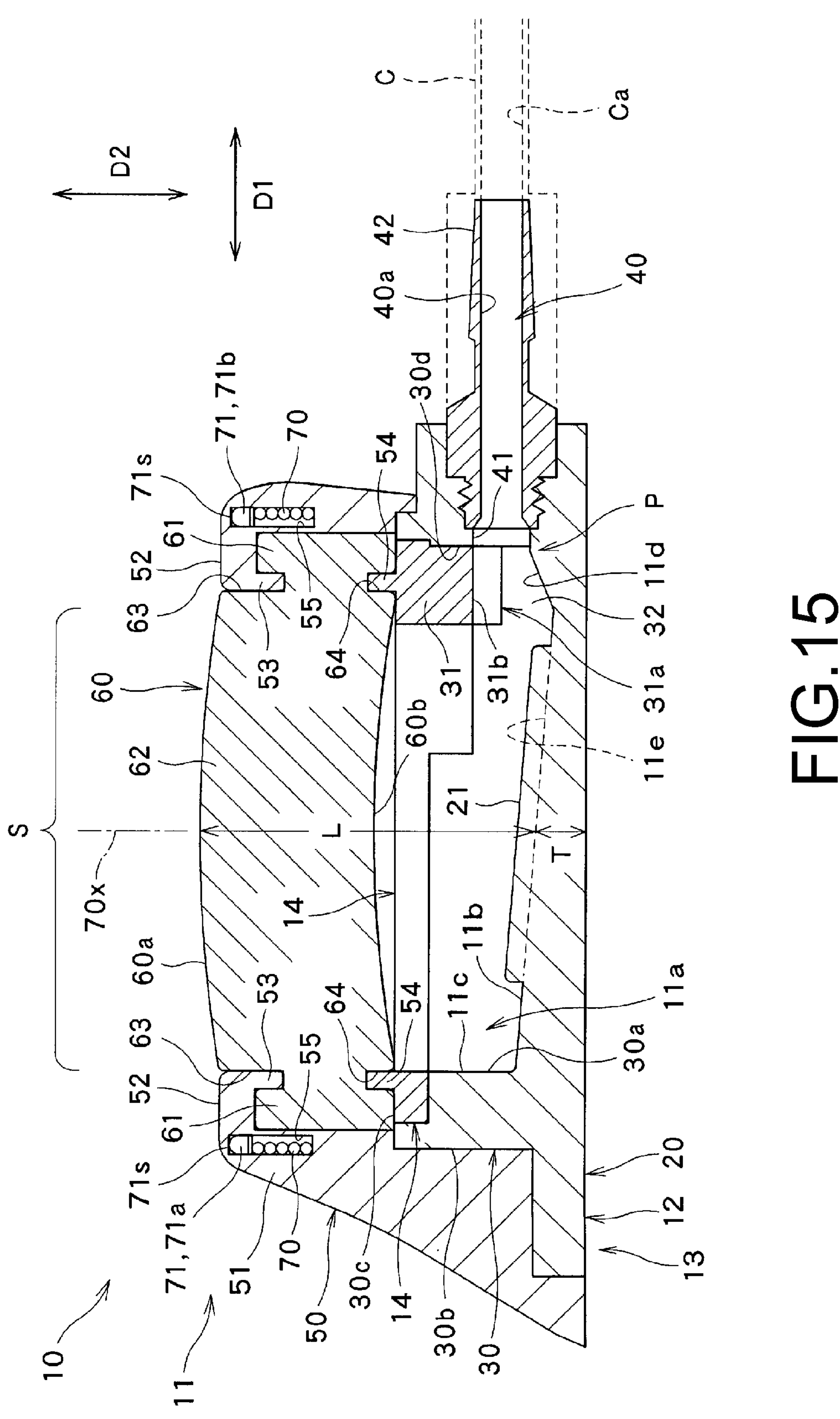
FIG. 15 is a cross-sectional view of the access port taken along line IV-IV in FIG. 14.

In addition, the access ports 10 and 100 according to the first and second examples may have only one metal coil 70 as illustrated in FIG. 14. In this example, it is preferable that two or more light emitters 71*a* and 71*b* are electrically connected to the metal coil 70, and the light emitters 71*a* and 71*b* are disposed to surround the diaphragm body 60 or 160. In this example, as illustrated in FIGS. 14 and 15, the metal coil 70 may be arranged to surround the liquid storage portion 11*a* when observed from the direction parallel to the direction in which the side wall portion 30 extends from the bottom wall portion 20.

Figure 16:
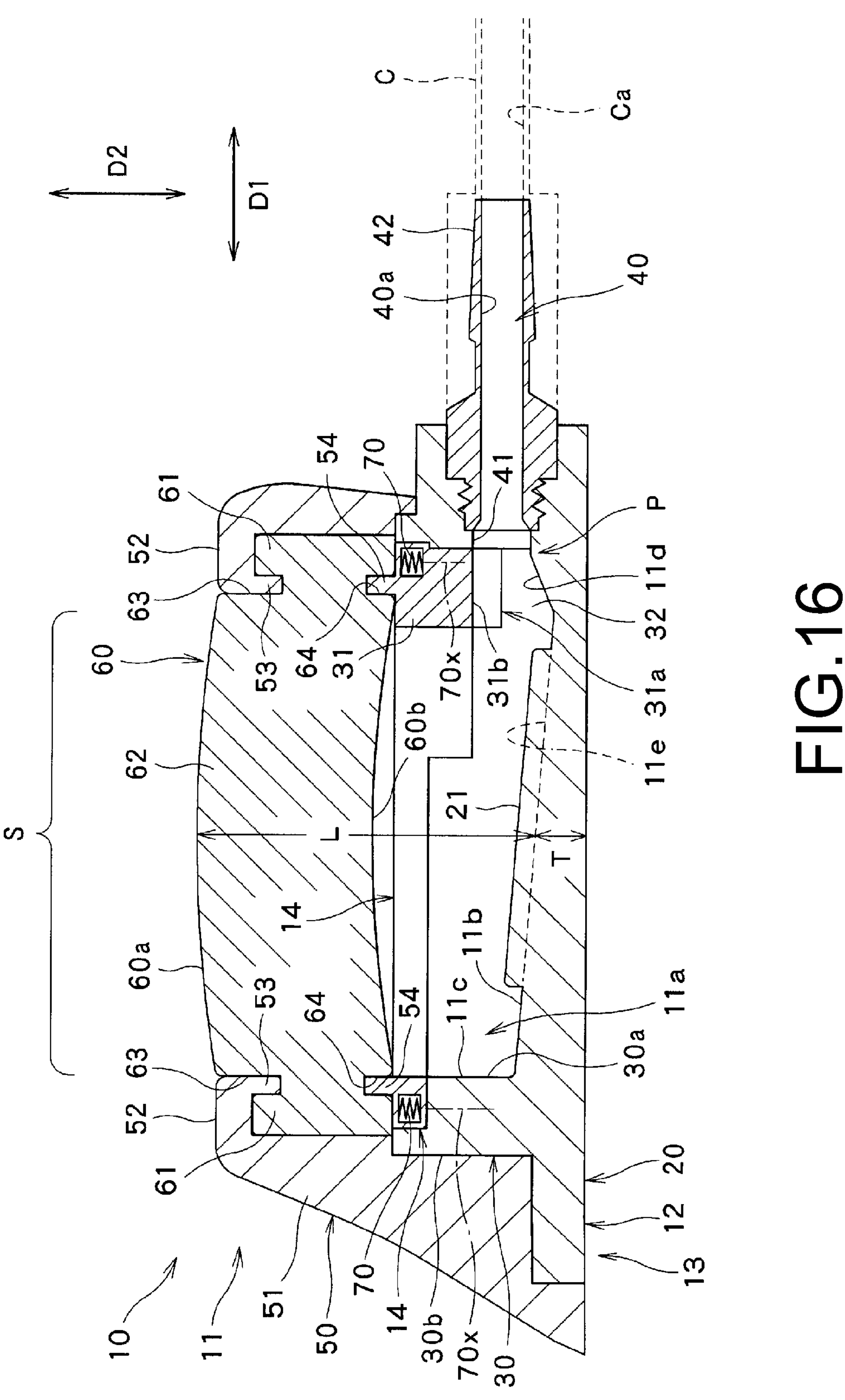
FIG. 16 is a view corresponding to FIG. 4, and is a cross-sectional view explaining another modification of the access port.

The metal coil 70 may be incorporated in any portion of the port body 11. For example, as illustrated in FIG. 16, the metal coil 70 may be incorporated in the base member 12. In this example, the metal coil 70 may be incorporated in the side wall portion 30. In this example, as illustrated in FIG. 16, the base member 12 may be configured by the bottom member 13 and an annular member 14 separate from the bottom member 13, and the metal coil 70 may be incorporated in the annular member 14. In this way, it is easy to incorporate the metal coil 70 in the base member 12 so that the metal coil 70 does not come into contact with the body fluid of the patient or the drug stored in the liquid storage portion 11*a*.

In addition, the light emitting surface 71*s* of the light emitter 71 may be exposed to the surface of the access port 10 or 100 (the surface opposite to the surface facing the liquid storage portion 11*a*). In this example, it is easy to deliver the light emitted from the light emitter 71 to the skin surface of the patient in a state where the access port 10 or 100 is embedded under the skin of the patient. The light emitted from the light emitter 71 is easily perceived by the person around the patient. When the light emitting surface 71*s* of the light emitter 71 is exposed to the surface of the access port 10 or 100, it is desirable that, in the space that stores the circuit 74 including the metal coil 70 and the light emitter 71, a portion that stores the metal member including the metal coil 70 be sealed in a liquid-tight manner. As a result, contact between the metal member and a body fluid of a patient in which the access port 10 or 100 is embedded, and a drug or the like stored in the liquid storage portion 11*a* is prevented.

As described above, according to the first and second examples, the access port 10 or 100 is an access port used by being connected to the catheter C, and includes the port body 11 or 111 including the liquid storage portion 11*a* and the diaphragm body 60 or 160 held by the port body 11 or 111 and covering the liquid storage portion 11*a*. The port body 11 or 111 includes the connection passage 40 that is connected to the liquid storage portion 11*a* and allows the liquid storage portion 11*a* to communicate with the inside of the catheter C. In the cross-section along the axial direction D1 of the connection passage 40 at the connection position P where the connection passage 40 is connected to the liquid storage portion 11*a*, the length L in the direction perpendicular to the axial direction D1 between the surface 60*a* or 160*a* of the diaphragm body 60 or 160 on the side opposite to the liquid storage portion 11*a* and the inner surface of the liquid storage portion 11*a* gradually decreases as it proceeds away from the connection position P in the inclined region S exceeding half of the liquid storage portion 11*a* along the axial direction D1.

According to such an access port 10 or 100, in the inclined region S, the tip of the microcatheter or the guide wire inserted into the liquid storage portion 11*a* along the direction perpendicular to one side surface 60*a* or 160*a* of the diaphragm body is easily guided in the direction toward the connection position P (in the direction toward the connection passage 40). In addition, since the inclined region S is formed in the region exceeding half of the liquid storage portion 11*a* along the axial direction D1 even when the tip of the microcatheter or the guide wire inserted into the liquid storage portion 11*a* reaches a position deviated from the center of the liquid storage portion 11*a*, the tip of the microcatheter or the guide wire is easily guided in a direction toward the connection passage 40. As described above, the microcatheter and the guide wire can be stably and easily inserted into the connection passage 40.

In addition, in the access ports 10 and 100 according to the first and second examples, the inclined region S includes a half region of the liquid storage portion 11*a* on the side away from the connection position P. As a result, even when the tip of the microcatheter or the guide wire inserted into the liquid storage portion 11*a* reaches a position farther from the connection position P than the center of the liquid storage portion 11*a*, the tip is easily guided in a direction toward the connection passage 40.

In the access port 10 according to the first example, the inner surface of the liquid storage portion 11*a* in the inclined region S is inclined with respect to the axial direction D1 in the cross-section along the axial direction D1 of the connection passage 40. The inclined region S is formed by such a liquid storage portion 11*a*.

In the access port 10 according to the first example, the inner surface of the port body 11 includes the bottom surface 11*b* that forms (defines) the liquid storage portion 11*a* and the side surface 11*c* that extends from the bottom surface 11*b* to form (define) the liquid storage portion 11*a*, and the bottom surface 11*b* is inclined with respect to the axial direction D1. The inclined region S is formed by such a bottom surface 11*b*.

In the access port 10 according to the first example, the port body 11 has the bottom wall portion 20 that forms the bottom surface 11*b* of the liquid storage portion 11*a*. The thickness T of the bottom wall portion 20 gradually decreases as it approaches the connection position P along the axial direction D1. As a result, the bottom surface 11*b* is inclined with respect to the axial direction D1.

In addition, in the access port 10 according to the first example, the bottom surface 11*b* of the port body 11 includes the connection bottom surface 11*d* connected to the side wall surface 30*d* to which the connection passage 40 is open, and the main bottom surface 11*e* located on the side away from the connection position P with respect to the connection bottom surface 11*d* in the axial direction D1. The main bottom surface 11*e* is inclined with respect to the axial direction D1 toward the side away from the diaphragm body 60 as it approaches the connection position P. The inclined region S is formed by such a main bottom surface 11*e*.

In addition, in the access port 10 according to the first example, the connection bottom surface 11*d* is inclined with respect to the axial direction D1 toward the side closer to the diaphragm body 60 as it approaches the connection position P. With such a connection bottom surface 11*d*, the tip of the microcatheter or the guide wire guided toward the connection position P by the main bottom surface 11*e* can be guided in a direction toward the diaphragm body 60 as it further approaches the connection position P (that is, toward the opening 41 of the connection passage 40 formed in the side wall portion 30). As a result, the microcatheter and the guide wire can be more stably and easily inserted into the connection passage 40.

In the access port 10 according to the first example, the port body 11 includes the bottom wall portion 20 that forms the bottom surface 11*b* of the liquid storage portion 11*a* and the side wall portion 30 that forms the side surface 11*c* of the liquid storage portion 11*a*. The side wall portion 30 has the protruding portion 31 provided to be spaced apart from the bottom wall portion 20 and having the facing guide surface 31*a* facing the bottom surface 11*b*. The connection passage 40 is open to the side surface 11*c* at a position between the facing guide surface 31*a* and the bottom surface 11*b*.

The facing guide surface 31*a* of the protruding portion 31 and the region of the bottom surface 11*b* facing the facing guide surface 31*a* allow the tip of the microcatheter or the guide wire to be efficiently directed to the connection passage opening 41. Specifically, the movable region of the tip is limited between the facing guide surface 31*a* and the bottom surface 11*b*, and the tip is easily directed to the opening 41 of the connection passage 40 open to a position between the facing guide surface 31*a* and the bottom surface 11*b*.

In addition, in the access port 10 according to the first example, the facing guide surface 31*a* has the concave surface 31*b* recessed away from the bottom surface 11*b* at its central portion in the width direction D3 perpendicular to both the axial direction D1 and the direction in which the facing guide surface 31*a* faces the bottom surface 11*b*. When the tip of the microcatheter or the guide wire enters the region surrounded by such a concave surface 31*b*, the movable range of the tip is limited to the region surrounded by the concave surface 31*b*. Therefore, the tip is more easily directed to the opening 41 of the connection passage 40.

In addition, in the access port 10 according to the first example, the concave surface 31*b* is connected to the wall surface 40*a* forming (defining) the connection passage 40. As a result, it is easy to direct the tip of the microcatheter or the guide wire moving toward the connection passage opening 41 along the concave surface 31*b* into the connection passage 40. That is, the possibility that the tip interferes with the side wall surface 30*d* to which the connection passage opening 41 is open to be prevented from entering the connection passage 40 is reduced.

In addition, in the access port 10 according to the first example, the inner surface of the port body 11 includes the connection bottom surface 11*d* provided at a position facing the facing guide surface 31*a*, and the main bottom surface 11*e* located on the side away from the connection position P with respect to the connection bottom surface 11*d* in the axial direction D1. The main bottom surface 11*e* is inclined with respect to the axial direction D1 toward the side away from the diaphragm body 60 as it approaches the connection position P. The connection bottom surface 11*d* is inclined with respect to the axial direction D1 toward the side closer to the diaphragm body 60 as it approaches the connection position P. Since the facing guide surface 31*a* is provided to face such a connection bottom surface 11*d*, the movable region of the tip of the microcatheter or the guide wire narrows as it approaches the connection position P, and the tip is easily directed to the connection passage 40 open to a position between the facing guide surface 31*a* and the bottom surface 11*b*.

In the access port 10 according to the first example, the port body 11 includes the base member 12 that forms the bottom surface 11*b* and the side surface 11*c* of the liquid storage portion 11*a*, and the lid member 50 that is fixed to the base member 12 so that the diaphragm body 60 is held between the base member 12 and the lid member 50. The base member 12 includes the bottom member 13 that forms at least the bottom surface 11*b*, and the annular member 14 that is supported by the bottom member 13 to surround the liquid storage portion 11*a*. The annular member 14 has the protruding portion 31 provided to correspond to the connection position P and protrude toward the liquid storage portion 11*a*. By forming the protruding portion 31 on the annular member 14 manufactured separately from the bottom member 13 in this manner, it is easy to provide the protruding portion 31 on the side wall portion 30.

In the access port 10 according to the first example, the annular member 14 is made of an X-ray opaque material. As a result, even in a state where the access port 10 is embedded under the skin of the patient, it is possible to grasp the region surrounded by the annular member 14 (that is, a region where a puncture needle inserting a microcatheter or a guide wire into the liquid storage portion 11*a* is to be inserted) using the X-ray imaging technology.

In the access port 10 according to the first example, the port body 11 includes the bottom wall portion 20 that forms the bottom surface 11*b* of the liquid storage portion 11*a* and the side wall portion 30 that extends from the bottom wall portion 20 to form the side surface 11*c* of the liquid storage portion 11*a*. The side wall portion 30 includes a pair of flat wall portions 32 and 32 provided side by side in its circumferential direction. The connection passage 40 is open to the side surface 11*c* at a position between the pair of flat wall portions 32 and 32. In addition, the pair of flat wall portions 32 and 32 forms tapered side surfaces extending linearly and tapered toward the connection passage 40 when observed from the direction parallel to the direction in which the side wall portion 30 extends from the bottom wall portion 20.

With such a pair of flat wall portions 32 and 32, the tip of the microcatheter or the guide wire can be efficiently directed to the connection passage 40. Specifically, due to the pair of flat wall portions 32 and 32, the movable region of the tip is narrowed as it approaches the connection passage 40 and the tip is guided toward the connection passage 40.

In the access port 10 according to the first example, the port body 11 includes the bottom wall portion 20 that forms the bottom surface 11*b* of the liquid storage portion 11*a* and the side wall portion 30 that extends from the bottom wall portion 20 to form the side surface 11*c* of the liquid storage portion 11*a*. The side wall portion 30 includes a pair of flat wall portions 32 and 32 arranged in its circumferential direction, and the connection passage 40 is open to the side surface 11*c* at a position between the pair of flat wall portions 32 and 32. The bottom wall portion 20 includes the guide rib 21 linearly extending toward the connection position P when observed from the direction parallel to the direction in which the side wall portion 30 extends from the bottom wall portion 20. According to such an access port 10, with the guide rib 21, the tip of the microcatheter or the guide wire inserted into the liquid storage portion 11*a* can be efficiently guided toward the connection position P.

In the access port 10 according to the first example, the port body 11 includes the bottom wall portion 20 that forms the bottom surface 11*b* of the liquid storage portion 11*a* and the side wall portion 30 that extends from the bottom wall portion 20 to form the side surface 11*c* of the liquid storage portion 11*a*. The diaphragm body 60 is formed with the annular holding groove 63 which extends in the direction parallel to the direction in which the side wall portion 30 extends from the bottom wall portion 20 and is open to the side opposite to the liquid storage portion 11*a*. In addition, the port body 11 has the annular holding protrusion portion 53 that protrudes in the direction parallel to the direction in which the side wall portion 30 extends from the bottom wall portion 20. By fitting the annular holding protrusion portion 53 into the annular holding groove 63, the possibility that the diaphragm body 60 falls off from the port body 11 due to the force applied to the diaphragm body 60 when the puncture needle is inserted into the diaphragm body 60 or when the puncture needle is pulled out from the diaphragm body 60 is reduced.

In the access port 100 according to the second example, the port body 111 includes the surface layer member 115 that forms the inner surface of the liquid storage portion 11*a* and the connection passage 40. The surface layer member 115 connects the inner surface of the liquid storage portion 11*a* and the connection passage 40 seamlessly. This reduces the possibility that the tip of the microcatheter or the guide wire interferes with the inner surface of the liquid storage portion 11*a* or the connection port 117 and is prevented from entering the connection passage 40.

In the access port 100 according to the second example, the surface layer member 115 is made of metal. As a result, even in a state where the access port 100 is embedded under the skin of the patient, the position of the liquid storage portion 11*a* formed by the surface layer member 115 (that is, a region into which a puncture needle inserting a microcatheter or a guide wire into the liquid storage portion 11*a* is to be inserted) can be grasped using the X-ray imaging technology.

In the access port 100 according to the second example, in the cross-section perpendicular to the axial direction D1 of the connection passage 40, the inner surface of the port body 111 is inclined with respect to the surface 160*b* of the diaphragm body 160 facing the inner surface of the surface layer member body portion 116 to approach the diaphragm body 160 on both outer sides in the direction D4 along the surface 160*b* facing the inner surface. More specifically, in the cross-section perpendicular to the axial direction D1 of the connection passage 40, the inner surface 116*a* of the port body 111 extends in a U-shape. The inner surface 116*a* of the port body 111 allows the movable region of the tip of the microcatheter or the guide wire to be narrowed and the tip is easily directed to the connection passage 40.

In addition, in the access port 100 according to the second example, in the cross-section of the connection passage 40 along the axial direction D1, the surface 160*a* of the diaphragm body 160 on the side opposite to the liquid storage portion 11*a* is inclined with respect to the axial direction D1. The inclined region S is formed in the access port 100 by such a surface 160*a*. The tip of the microcatheter or the guide wire inserted into the liquid storage portion 11*a* along a direction perpendicular to the surface 160*a* on the opposite side of the diaphragm body 160 is easily guided in a direction toward the connection passage 40.

In addition, in the access port 100 according to the second example, the surface 160*a* of the diaphragm body 160 on the side opposite to the liquid storage portion 11*a* has the first surface 160*c* located on the side away from the connection position P in the axial direction D1, and the second surface 160*d* located on the side closer to the connection position P in the axial direction D1 with respect to the first surface 160*c* and inclined with respect to the first surface 160*c*. The length Lc of the first surface 160*c* along the axial direction D1 is longer than the length Ld of the second surface 160*d* along the axial direction D1. Further, the first surface 160*c* is inclined with respect to the axial direction D1 toward the side away from the inner surface of the liquid storage portion 11*a* as it approaches the connection position P in the axial direction D1. The inclination angle of the first surface 160*c* with respect to the axial direction D1 is larger than the inclination angle of the second surface 160*d* with respect to the axial direction D1.

Since the inclination angle of the first surface 160*c* is larger than the inclination angle of the second surface 160*d*, the position of the first surface 160*c* can be grasped even in a state where the access port 100 is embedded under the skin of the patient. In addition, since the length Lc of the first surface 160*c* is longer than the length Ld of the second surface 160*d*, the first surface 160*c* (a region into which a puncture needle inserting a microcatheter or a guide wire into the liquid storage portion 11*a* is to be inserted) can be widely secured.

In the access ports 10 and 100 according to the first and second examples, the port body 11 or 111 has the built-in metal coil 70. As a result, the position of the access port 10 or 100 embedded under the skin of the patient can be grasped using the magnetic field generation device 80 or an X-ray imaging technique.

In addition, in the access ports 10 and 100 according to the first and second examples, the port body 11 or 111 includes at least two metal coils 70*a* and 70*b* provided to be separated from each other at positions around the liquid storage portion 11*a*. As a result, the position of the access port 10 or 100 embedded under the skin of the patient can be grasped more accurately using the magnetic field generation device 80 or an X-ray imaging technique.

In addition, in the access ports 10 and 100 according to the first and second examples, the surface 60*a* or 160*a* of the diaphragm body 60 or 160 on the side opposite to the liquid storage portion 11*a* is exposed to a region between the two metal coils 70*a* and 70*b*. As a result, the position of the diaphragm body 60 or 160 of the access port 10 or 100 embedded under the skin of the patient (that is, a region into which a puncture needle inserting a microcatheter or a guide wire into the liquid storage portion 11*a* is to be inserted) can be grasped more accurately using the magnetic field generation device 80 or the X-ray imaging technology.

In the access ports 10 and 100 according to the first and second examples, the port body 11 or 111 includes at least two light emitters 71*a* and 71*b* electrically connected to the metal coils 70*a* and 70*b*, respectively. As a result, when a magnetic field is applied to the vicinity of the access port 10 or 100, a current flows through the circuit 74 including the metal coils 70*a* and 70*b* and the light emitters 71*a* and 71*b*, and the light emitters 71*a* and 71*b* emit light. The position of the access port 10 or 100 embedded under the skin of the patient can be grasped by the light emitted from the light emitters 71*a* and 71*b*.

In addition, in the access port 10 or 100 according to the modification, the light emitting surfaces 71*s* of the at least two light emitters 71*a* and 71*b* are exposed. In this way, it is easy to deliver the light emitted from the light emitter 71 to the skin surface of the patient in a state where the access port 10 is embedded under the skin of the patient. That is, the light emitted from the light emitter 71 is easily perceived by the person around the patient.

In the access port 10 according to the modification, the port body 11 includes the bottom wall portion 20 that forms the bottom surface 11*b* of the liquid storage portion 11*a* and the side wall portion 30 that forms the side surface 11*c* of the liquid storage portion 11*a*. The at least two metal coils 70*a* and 70*b* are incorporated in the side wall portion 30. As a result, the position of the liquid storage portion 11*a* can be grasped more accurately.

In addition, in the access ports 10 and 100 according to the first and second examples, the axis 70*x* of each of the metal coils 70*a* and 70*b* extends in the direction parallel to the direction in which the side wall portions 30 and 130 extends from the bottom wall portions 20 and 120. The base members 12 and 112 and the lid members 50 and 150 constituting the port body 11 or 111 have portions extending along the direction in which the side wall portion 30 extends from the bottom wall portion 20. Therefore, when the extension direction of the axis 70*x* is along the direction in which the side wall portions 30 and 130 extends from the bottom wall portions 20 and 120, it is possible to suppress an increase in the size of the port body 11 or 111 due to the incorporation of the metal coil 70 in the port body 11 or 111.

Although the plurality of examples and the modifications thereof have been described above, it is apparent that a plurality of configurations described as different examples or different modifications can be appropriately combined.

The invention claimed is:

1. An access port to be connected to a catheter, the access port comprising:

a port body including a liquid storage portion; and a diaphragm body held by the port body and covering the liquid storage portion, wherein the port body includes a connection passage connected to the liquid storage portion to allow the liquid storage portion to communicate with an inside of the catheter, and in a cross-section along an axial direction of the connection passage at a connection position where the connection passage is connected to the liquid storage portion, a length in a direction perpendicular to the axial direction between a surface of the diaphragm body opposite to the liquid storage portion and an inner surface of the liquid storage portion gradually decreases as the inner surface proceeds away from the connection position in an inclined region exceeding half of the liquid storage portion along the axial direction;

a surface of the diaphragm body opposite to the liquid storage portion has a first surface located on a side away from the connection position in the axial direction, and a second surface located on a side closer to the connection position in the axial direction with respect to the first surface and inclined with respect to the first surface, wherein the first surface and the second surface intersect on a bent portion which extends linearly along a second direction perpendicular to the axial direction to create an angle therebetween;

a length of the first surface along the axial direction is longer than a length of the second surface along the axial direction, the first surface is inclined with respect to the axial direction toward a side away from the inner surface of the liquid storage portion as the first surface approaches the connection position in the axial direction, and an inclination angle of the first surface with respect to the axial direction is larger than an inclination angle of the second surface with respect to the axial direction.

2. The access port according to claim 1, wherein the port body includes a bottom wall portion that forms a bottom surface of the liquid storage portion and a side wall portion that forms a side surface of the liquid storage portion, the side wall portion includes a protruding portion provided to be spaced apart from the bottom wall portion and having a facing guide surface facing the bottom surface, and the connection passage opens to the side surface at a position between the facing guide surface and the bottom surface.

3. The access port according to claim 2, wherein the facing guide surface has a concave surface recessed away from the bottom surface at a central portion of the facing guide surface in a width direction perpendicular to both the axial direction and a direction in which the facing guide surface faces the bottom surface.

4. The access port according to claim 1, wherein the port body includes a bottom wall portion that forms a bottom surface of the liquid storage portion and a side wall portion that extends from the bottom wall portion to form a side surface of the liquid storage portion, the side wall portion includes a pair of flat wall portions arranged side by side in a circumferential direction of the side wall portion, the connection passage opens to the side surface at a position between the pair of flat wall portions, and the bottom wall portion includes a guide rib extending linearly toward the connection position when observed from a direction parallel to a direction in which the side wall portion extends from the bottom wall portion.

5. The access port according to claim 1, wherein the port body includes a surface layer member that forms an inner surface of the liquid storage portion and the connection passage, and the surface layer member connects the inner surface of the liquid storage portion and the connection passage seamlessly.

6. The access port according to claim 1, wherein, in a cross-section perpendicular to the axial direction of the connection passage, an inner surface of the port body is inclined with respect to a lower surface of the diaphragm body facing the inner surface of the port body to approach the diaphragm body on both outer sides in a direction along the lower surface.

7. The access port according to claim 6, wherein the inner surface extends in a U-shape in the cross-section perpendicular to the axial direction of the connection passage.

8. The access port according to claim 1, wherein the port body has a built-in metal coil.

9. The access port according to claim 1, wherein the port body includes at least two metal coils provided to be spaced apart from each other at positions around the liquid storage portion, and at least two light emitters electrically connected to the metal coils.

10. The access port according to claim 9, wherein the port body includes a bottom wall portion that forms a bottom surface of the liquid storage portion and a side wall portion that forms a side surface of the liquid storage portion, and the at least two metal coils are incorporated in the side wall portion.

* * * * *